United States Patent
Hardt et al.

(10) Patent No.: US 9,919,029 B2
(45) Date of Patent: Mar. 20, 2018

(54) METHODS AND PHARMACEUTICAL COMPOSITIONS FOR THE TREATMENT OF BACTERIAL INFECTIONS

(71) Applicants: INSERM (INSTITUT NATIONAL DE LA SANTE ET DE LA RECHERCHE MEDICALE), Paris (FR); UNIVERSITE DE DROIT ET DE LA SANTE DE LILLE 2, Lille (FR); CENTRE NATIONAL DE LA RECHERCHE SCIENTIFIQUE (CNRS), Paris (FR); INSTITUT PASTEUR DE LILLE, Lille (FR); UNIVERSITE DE LILLE 1 SCIENCES ET TECHNOLOGIES, Villeneuve d'Ascq (FR); ETH ZURICH, Zurich (CH); UNIVERSIDAD DE LA REPUBLICA, Montevideo (UY)

(72) Inventors: Wolf-Dietrich Hardt, Zurich (CH); Patrick Kaiser, Zurich (CH); Jean-Claude Sirard, Lille (FR); Christophe Carnoy, Lille (FR); Delphine Fougeron, Lille (FR); Jose Alejandro Chabalgoity, Montevideo (UY); Natalia Munoz, Montevideo (UY)

(73) Assignees: INSERM (Institut National de la Sante et de la Recherche Medicale), Paris (FR); Universite de Droit et de la Sante de Lille 2, Lille (FR); Centre National de la Recherche Scientifique (CNRS), Paris (FR); Institut Pasteur de Lille, Lille (FR); Universite de Lille 1 Sciences et Technologies, Lille (FR); ETH Zurich, Zurich (CH); Universidad de la Republica, Montevideo (UY)

( * ) Notice: Subject to any disclaimer, the term of this patent is extended or adjusted under 35 U.S.C. 154(b) by 0 days.

(21) Appl. No.: 14/906,747

(22) PCT Filed: Jul. 25, 2014

(86) PCT No.: PCT/EP2014/066007
§ 371 (c)(1),
(2) Date: Jan. 21, 2016

(87) PCT Pub. No.: WO2015/011254
PCT Pub. Date: Jan. 29, 2015

(65) Prior Publication Data
US 2016/0151453 A1    Jun. 2, 2016

(30) Foreign Application Priority Data

Jul. 26, 2013 (EP) .................................. 13306086

(51) Int. Cl.
| | |
|---|---|
| A61K 38/16 | (2006.01) |
| A61K 31/505 | (2006.01) |
| A61K 31/42 | (2006.01) |
| A61K 31/43 | (2006.01) |
| A61K 45/06 | (2006.01) |
| A61K 31/635 | (2006.01) |

(52) U.S. Cl.
CPC ............ *A61K 38/164* (2013.01); *A61K 31/42* (2013.01); *A61K 31/43* (2013.01); *A61K 31/505* (2013.01); *A61K 31/635* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 2010/0104516 A1* | 4/2010 | Yu | ......................... | A61K 38/164 514/1.1 |
| 2011/0110962 A1* | 5/2011 | Sirard | .................... | A61K 39/39 424/184.1 |

FOREIGN PATENT DOCUMENTS

| | | | |
|---|---|---|---|
| WO | 2007/050606 A2 | | 5/2007 |
| WO | WO2011/161491 | * | 12/2011 |
| WO | 2012/152898 A1 | | 11/2012 |

OTHER PUBLICATIONS

Abgueguen et al. ("Amoxicillin is Effective against penicillin-resistant *Streptococcus pneumoniae* strains in a mouse model stimulating human pharmacokinetics"; Antimicrob Agents Chemother. Jan. 2007;51(1): 208-214).*
Caballero (Annals of Intensive Car 2011, 1:48).*
E. Musie, "Without Antibiotics, Toll-Like Receptor 4 (TLR4) Stimulation Before Challenge Protects Mice in a Lethal Model of Systemic *Staphylococcus aureus*", Nov. 27, 2008, Web.

\* cited by examiner

*Primary Examiner* — James H Alstrum-Acevedo
*Assistant Examiner* — Tara L Martinez
(74) *Attorney, Agent, or Firm* — Whitham Curtis & Cook, PC

(57) ABSTRACT

The present invention relates to methods and pharmaceutical compositions for the treatment of bacterial infections. In particular, the present invention relates to a Toll-like receptor (TLR) agonist for use in a method for the treatment of a bacterial infection in a subject in need thereof wherein the TLR agonist is administered to the subject in combination with at least one antibiotic.

13 Claims, 9 Drawing Sheets

Figure 1:
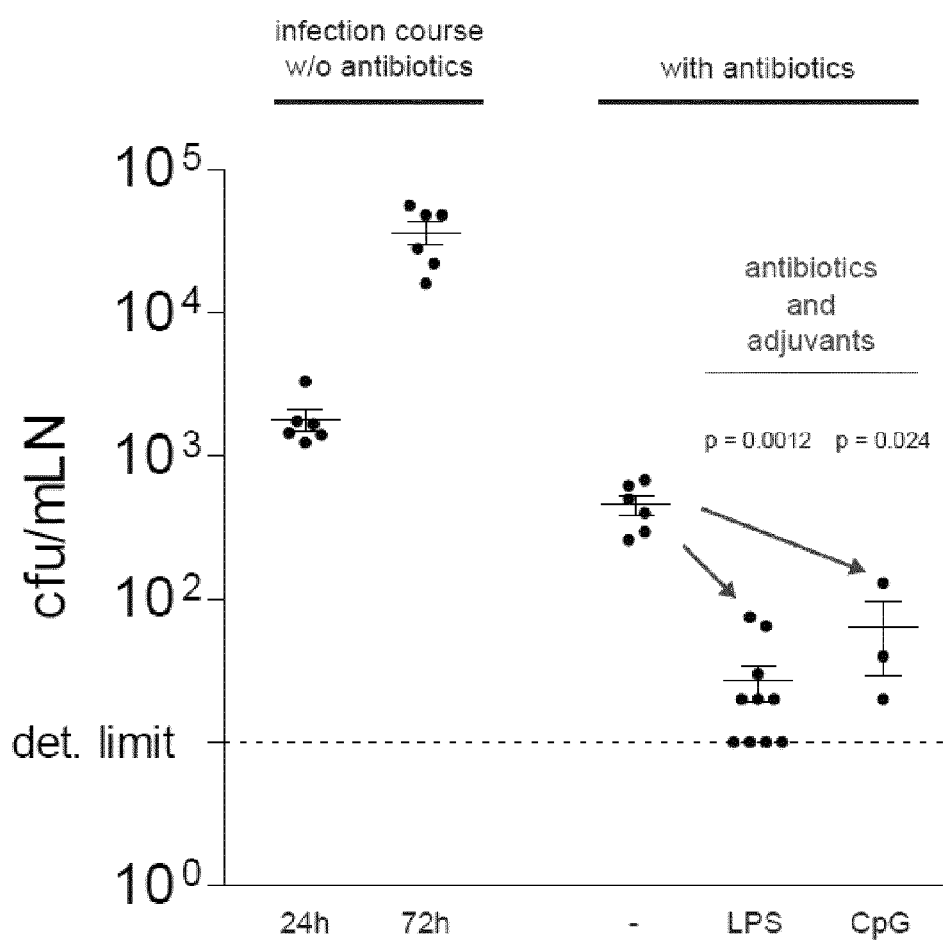

METHODS AND PHARMACEUTICAL COMPOSITIONS FOR THE TREATMENT OF BACTERIAL INFECTIONS

FIELD OF THE INVENTION

The present invention relates to methods and pharmaceutical compositions for the treatment of bacterial infections.

BACKGROUND OF THE INVENTION

Bacterial infections are a major health problem and pose a large economic burden on our society. Bacterial infections can be caused by a wide range of bacteria, resulting in mild to life-threatening illnesses that require immediate intervention. Common bacterial infections include for example pneumonia, ear infections, diarrhea, urinary tract infections, and skin disorders.

For example, *Streptococcus pneumoniae* (pneumococcus) causes respiratory tract infections among infants and the elderly worldwide. Capsular polysaccharide is the main virulence factor, and its composition defines 91 serotypes of pneumococcus. Certain serotypes colonize asymptomatically the human nasopharynx representing a reservoir for inter-individual transmission of the bacteria. In some individuals colonization may progress to pneumococcal pneumonia and invasive disease. Other examples include *Salmonella enterica* which cause significant morbidity and mortality worldwide. The predominant *Salmonella enterica* serovars causing disease in humans are Typhi, Paratyphi A and B, and *Typhimurium*. The Typhi and Paratyphi serovars are strict human pathogens and cause typhoid fever, while the non-typhoidal *Salmonella enterica* subspecies *Typhimurium* results primarily in gastroenteritis in humans.

The treatment of bacterial infections is most often achieved by using antibiotics which either aim at killing invading bacteria (bactericide mode of action) or inhibiting their growth (bacteriostatic mode of action) without harming the host. Antibiotic effectiveness depends on mechanism of action, drug distribution, site of infection, immune status of the host, and resistance factors of bacteria. Antibiotics work through several mechanisms; some inhibit the formation of bacterial cell walls. Others interrupt bacterial protein synthesis. Yet some others inhibit metabolism or interfere with DNA synthesis and/or cell membrane permeability.

It is however becoming more evident, that antibiotics do not always perform to the extent they should. Some infections cannot be cleared, even if the pathogen is sensitive to the used antibiotic. This inability to completely kill all bacteria poses a severe problem once the antibiotic treatment is stopped, as the infection relapses and the patients fall ill anew. Moreover, the constant antibiotic pressure and the natural competence of some strains results in frequent resistance to antibiotics. The increasing burden of antimicrobial resistance coupled with the decreasing number of antibiotics in development has urged for strategies to maximize the therapeutic index of existing antibiotics.

SUMMARY OF THE INVENTION

The present invention relates to methods and pharmaceutical compositions for the treatment of bacterial infections. In particular, the present invention relates to a Toll-like receptor (TLR) agonist for use in a method for the treatment of a bacterial infection in a subject in need thereof wherein the TLR agonist is administered to the subject in combination with at least one antibiotic.

DETAILED DESCRIPTION OF THE INVENTION

The present invention relates to a combination of a Toll-like receptor (TLR) agonist and an antibiotic for use in a method for the treatment of a bacterial infection in a subject in need thereof.

The present invention also relates to a TLR agonist for use in a method for enhancing the clinical efficacy of an antibiotic for clearing an infection in a subject in need thereof.

As used herein the expression "a method for enhancing the clinical efficacy of an antibiotic" refers to the fact that the TLR agonist of the invention improves clearance of the bacteria and recovery from the infection compared to the standalone antibiotic treatment. In particular, the combination of the antibiotic with the TLR agonist can enhance the capacity of host to repair the damages induced by infection before starting treatment. The combination of the invention could thus decrease the morbidity. According to the invention, the TLR agonist potentiates the activity of the antibiotic for the clearance of the bacterial infection. The term "potentiate", as used herein, means to enhance or increase at least one biological effect or activity of the antibiotic so that either (i) a given concentration or amount of the antibiotic results in a greater biological effect or activity when the antibiotic is potentiated than the biological effect or activity that would result from the same concentration or amount of the antibiotic when not potentiated; or (ii) a lower concentration or amount of the antibiotic is required to achieve a particular biological effect or activity when the antibiotic is potentiated than when the antibiotic is not potentiated; or (iii) both (i) and (ii). In particular, TLR agonists combined to antibiotics: —1—may impact on a specific niche that is not accessible to antibiotic (i.e. intracellular compartments of some cells), allowing antibiotics to work when combined to TLR agonists; —2—may impact on the recovery phase from antibiotic treatment of infection (tissue repair, restoration of physiological function of infected tissues); —3—may limit side effects (for example alteration of microbiota composition in gut, skin, respiratory tract . . . ) and —4—may restrain the development of antibiotic resistance (often due to acquisition of resistance by the microbiota bacteria).

In some embodiments, the infection is caused by gram-positive bacteria or gram-negative bacteria, including *Mycobacterium* species. Typically, the bacteria form small coccobacilli; small, round, ovoid rods; large, blunt-ended rods; small, slender, pleomorphic rods; ovoid to spherical rods; long, slender, flexible, spiral- or corkscrew-shaped rods; slender, short rods; curved rods with single polar flagellum, or Kidney bean-shaped rods.

In some embodiments, the bacterial infection is an infection of the gastrointestinal tract, an infection of the urogenital tract, an infection of the respiratory tract, like, for example rhinitis, tonsillitis, pharyngitis, bronchitis, pneumonia, an infection of the inner organs, like, for example, nephritis, hepatitis, peritonitis, endocarditis, meningitis, osteomyelitis, an infection of the eyes, the ears as well as a cutaneous and a subcutaneous infection, diarrhea, skin disorders, toxic shock syndrome, bacteraemia, sepsis, and tuberculosis.

In some embodiments, the bacteria are selected from the genus *Staphylococcus*, *Streptococcus*, *Pseudomonas*, *Escherichia*, *Salmonella*, *Helicobacter*, *Neisseria*, *Campylobacter*, *Chlamydia*, *Clostridium*, *Vibrio*, *Treponema*,

*Mycobacterium, Klebsiella, Actinomyces, Bacterioides, Bordetella, Borrelia, Brucella, Corynebacterium, Diplococcus, Enterobacter, Fusobacterium, Leptospira, Listeria, Pasteurella, Proteus, Rickettsia, Shigella, Sphaerophorus, Yersinia,* or combinations thereof. Examples of bacteria which cause bacterial respiratory tract infections include, but not limited to, *Chlamydia* species (e.g., *Chlamydia pneumoniae*), *Klebsiella species, Haemophilus influenzae,* Legionallaceae family, mycobacteria (e.g., *Mycobacterium tuberculosis*), Pasteurellaceae family, *Pseudomonas* species, *Staphylococcus* (e.g., methicillin resistant *Staphylococcus aureus* and *Staphylococcus pyrogenes*), *Streptococcus* (e.g., *Streptococcus enteritidis, Streptococcus Fasciae,* and *Streptococcus pneumoniae*). Examples of bacteria which cause intestinal infections include, but not limited to Bacteroidaceae family, *Campylobacter* species, *Chlamydia* species (e.g., *Chlamydia pneumoniae*), *Clostridium,* Enterobacteriaceae family (e.g., *Citrobacter* species, *Edwardsiella, Enterobacter aerogenes, Escherichia coli, Klebsiella* species, *Salmonella* species, and *Shigella flexneri*), Gardinella family, *Listeria* species, Pasteurellaceae family, *Pseudomonas* species, *Streptococcus* (e.g., *Streptococcus enteritidis, Streptococcus Fasciae,* and *Streptococcus pneumoniae*), Helicobacter Family.

In some embodiments the combination of the TLR agonist and the antibiotic is particularly suitable for the clearance of a bacterium resistant to this antibiotic. A bacterium that is not "sensitive" is considered "persistent" or "resistant". Persistence is a way by which a bacterium can survive exposure to an antibiotic. Here, the physiological state of the bacterium is modified such that the antibiotic cannot kill. This situation may explain why some bacteria (though considered sensitive by in vitro MIC testing) survive antibiotic treatment of a patient. These bacteria can carry on the infection during an antibiotic therapy and/or cause a relapse after the end of an antibiotic therapy. Resistance means that the bacterium can survive and proliferate in the presence of the antibiotic. Methods for assessing sensitivity typically involve determining the MIC by methods such as the broth microdilution method, agar dilution, and the agar disk diffusion method. The MIC may then be compared with a predefined "breakpoint", wherein a MIC greater than the breakpoint indicates that the bacterium is resistant to the agent and a MIC equal to or below the breakpoint indicates that the bacterium is sensitive to the agent. Sensitivity and/or resistance may be assessed according to the guidelines and methods well established. "Intrinsic resistance" means that a bacterial species is inherently resistant to the effects of an antibiotic. "Acquired resistance" means that a bacterial species, subtype, or strain has acquired a mechanism of resistance since the introduction of the antibiotic into use. Resistance may, for example, be acquired by mutation of a target gene, by overexpression of an efflux pump, etc.

As used herein the term "Toll like receptor (TLR)" has its general meaning in the art and describes a member of the Toll-like receptor family of proteins or a fragment thereof that senses a microbial product and/or initiates an innate or an adaptive immune response. Toll-like receptors (TLRs) are a family of germline-encoded transmembrane proteins that facilitate pathogen recognition and activation of the innate immune system. (Hoffmann J A et al., Science 284, 1313-1318 (1999); Rock F L et al., Proc Natl Acad Sci USA 95:588-593 (1998)). Toll-like receptors (TLRs) are pattern recognition receptors (PRRs), and are expressed by cells of the innate immune system, including macrophages, dendritic cells and NK cells. Toll-like Receptors include TLR1, TLR2, TLR3, TLR4, TLR5, TLR6, TLR7, TLR 8, TLR9, TLR10, TR11 and TLR12. Examples of known ligands for TLRs include gram positive bacteria (TLR-2), bacterial endotoxin (TLR-4), flagellin protein (TLR-5), bacterial DNA (TLR-9), double-stranded RNA and poly I:C (TLR-3), and yeast (TLR-2). Other ligands that bind to endocytic pattern recognition receptors, a scavenger receptor or a mannose-binding receptor may also be contemplated by the instant invention. TLRs engage conserved pathogen-derived ligands and subsequently activate the TLR/IL-1R signal transduction pathway to induce a variety of effector genes. (Medzhitov R et al., Moll Cell 2:253-258 (1998); Muzio M et al., J Exp Med 187:2097-2101 (1998)). Toll-like receptors (TLRs) represent an important group of PRRs that can sense PAMPs or MAMPs once in the body. They are widely expressed in blood, spleen, lung, muscle and intestines by many types of cells, notably dendritic cells (DCs) but also macrophages, epithelial cells, and lymphocytes. Whereas some TLRs located on the cell surface are specific for microbial lipids and proteins, others associated with endosomal compartments inside cells are specific for nucleic acids. Ligation of the TLRs by their specific ligands results in conformational changes in the receptors, leading to downstream signal transduction that primarily involves MyD88- and TRIF-dependent pathways. Except for TLR3, all other TLRs can signal through the MyD88 pathway to induce proinflammatory cytokines that involve activation of intracellular protein kinase cascades including IB kinase (IKK)-NF-B, and extracellular signal-regulated protein kinase (ERK), c-Jun N-terminal kinase (JNK) and p38 mitogen-activation protein kinases (MAPKs) The TRIF pathway, independent of MyD88, is utilized by both TLR3 and TLR4 and mediates the induction of type I interferons. TLR ligands are often found multiply in different types of pathogens.

The term "agonist" as used herein in referring to a TLR activating molecule, means a molecule that activates a TLR signaling pathway. As discussed above, a TLR signaling pathway is an intracellular signal transduction pathway employed by a particular TLR that can be activated by the TLR agonist. Common intracellular pathways are employed by TLRs and include, for example, NF-κB, Jun N-terminal kinase and mitogen-activated protein kinase. The TLR agonism for a particular compound may be assessed in any suitable manner. For example, assays for detecting TLR agonism of test compounds are described, for example, in U.S. Provisional Patent Application Ser. No. 60/432,650, filed Dec. 11, 2002, and recombinant cell lines suitable for use in such assays are described, for example, in U.S. Provisional Patent Application Ser. No. 60/432,651, filed Dec. 11, 2002.

In some embodiments, the TLR agonist is selected from the group consisting of TLR1, TLR2, TLR3, TLR4, TLR5, TLR6, TLR7, TLR8, TLR9, TLR10, TLR11, TLR12, or TLR13 agonists.

In some embodiments, the TLR agonist according to the invention is selected from the group consisting of low molecular weight molecules (e.g. a small organic molecule), biomolecules (e.g. lipid), peptides, polypeptides, antibodies, and nucleic acids (e.g. ODN or aptamers). Typically, the agonist is a natural compound or not.

TLR agonists are well known in the art (see e.g. Baxevanis CN, Voutsas IF, Tsitsilonis OE. Toll-like receptor agonists: current status and future perspective on their utility as adjuvants in improving anticancer vaccination strategies. Immunotherapy, 2013 May; 5(5):497-511. doi: 10.2217/imt.13.24; Shaherin Basith, Balachandran Manavalan, Gwang Lee, Sang Geon Kim, Sangdun Choi Toll-like receptor modulators: a patent review (2006-2010) Expert Opinion on Therapeutic Patents June 2011, Vol. 21, No. 6, Pages 927-944; 20. Heather L. Davis Chapter 26: TLR9 Agonists for Immune Enhancement of Vaccines, New Generation Vaccines, Fourth Edition; Jory R Baldridge, Patrick McGowan, Jay T Evans, Christopher Cluff, Sally Mossman, David Johnson, David Persing Taking a Toll on human disease: Toll-like receptor 4 agonists as vaccine adjuvants and monotherapeutic agents Expert Opinion on Biological Therapy July 2004, Vol. 4, No. 7, Pages 1129-1138.).

In some embodiments, the TLR agonist is a TLR1 agonist. Examples of TLR1 agonists include tri-acylated lipopeptides (LPs); phenol-soluble modulin; *Mycobacterium tuberculosis* LP; S-(2,3-bis(palmitoyloxy)-(2-RS)-propyl)-N-palmitoyl-(R)-Cys-(S)-Ser-(S)-Lys(4)-OH, trihydrochloride (Pam3Cys) LP which mimics the acetylated amino terminus of a bacterial lipoprotein and OspA LP from *Borrelia burgdorferi*.

In some embodiments, the TLR agonist is a TLR2 agonist. For example, the TLR2 agonist consists of a flagellin modification protein FlmB of *Caulobacter crescentus*; Bacterial Type III secretion system protein; invasin protein of *Salmonella*; Type 4 fimbrial biogenesis protein (PilX) of *Pseudomonas*; *Salmonella* SciJ protein; putative integral membrane protein of *Streptomyces*; membrane protein of *Pseudomonas*; adhesin of *Bordetella pertusis*; peptidase B of *Vibrio cholerae*; virulence sensor protein of *Bordetella*; putative integral membrane protein of *Neisseria meningitidis*; fusion of flagellar biosynthesis proteins FliR and FlhB of *Clostridium*; outer membrane protein (porin) of *Acinetobacter*; flagellar biosynthesis protein FlhF of Helicobacter; ompA related protein of *Xanthomonas*; omp2a porin of *Brucella* spp.; putative porin/fimbrial assembly protein (LHrE) of *Salmonella*; wbdKK of *Salmonella*; Glycosyltransferase involved in LPS biosynthesis; *Salmonella* putative permease. In some embodiments, the TLR2 agonist is selected form the group consisting of lipoprotein/lipopeptides (isolate from a variety of pathogens); peptidoglycan (isolated form Gram-positive bacteria); lipoteichoic acid (isolated from Gram-positive bacteria); lipoarabinomannan (isolated from mycobacteria); a phenol-soluble modulin (isolated from *Staphylococcus epidermidis*); glycoinositolphospholipids (isolated from *Trypanosoma Cruzi*); glycolipids (isolated from *Treponema maltophilum*); porins (isolated from *Neisseria*); zymosan (isolated from fungi) and atypical LPS (isolated form *Leptospira interrogans* and *Porphyromonas gingivalis*). The TLR2 agonist can also include at least one member selected from the group consisting of (see, PCT/US 2006/002906/WO 2006/083706; PCT/US 2006/003285/WO 2006/083792; PCTAJS 2006/041865; PCT/US 2006/042051). The TLR2 agonist can include at least a portion of a bacterial lipoprotein (BLP). The TLR2 agonist can be a bacterial lipoprotein, such as Pam2Cys (S-[2,3-bis(palmitoyloxy)propyl]cysteine), Pam3Cys ([Palmitoyl]-Cys((RS)-2,3-di(palmitoyloxy)-propyl cysteine) or *Pseudomonas aeruginosa* Opr1 lipoprotein (Opr1). A bacterial lipoprotein that activates a TLR2 signaling pathway (a TLR2 agonist) is a bacterial protein that includes a palmitoleic acid (Omueti, K. O., et al, J. Biol. Chem. 280: 36616-36625 (2005)).

In some embodiments, the TLR agonist is a TLR3 agonist. For example, TLR3 agonists include naturally-occurring double-stranded RNA (dsRNA); synthetic ds RNA; and synthetic dsRNA analogs; and the like (Alexopoulou et al, 2001). An exemplary, non-limiting example of a synthetic dsRNA analog is Poly(I:C).

In some embodiments, the TLR agonist of the invention is a TLR4 agonist. Various TLR4 agonists are known in the art, including Monophosphoryl lipid A (MPLA), in the field also abbreviated to MPL, referring to naturally occurring components of bacterial lipopolysaccharide (LPS); refined detoxified endotoxin. For example, MPL is a derivative of lipid A from *Salmonella minnesota* R595 lipopolysaccharide (LPS or endotoxin). While LPS is a complex heterogeneous molecule, its lipid A portion is relatively similar across a wide variety of pathogenic strains of bacteria. MPL, used extensively as a vaccine adjuvant, has been shown to activate TLR4 (Martin M. et al., 2003. Infect Immun. 71(5): 2498-507; Ogawa T. et al., 2002. Int Immunol. 14(11):1325-32). TLR4 agonists also include natural and synthetic derivatives of MPLA, such as 3-de-O-acylated monophosphoryl lipid A (3D-MPL), and MPLA adjuvants available from Corixa Corporation (Seattle, Wash.; see U.S. Pat. Nos. 4,436,727; 4,436,728; 4,987,237; 4,877,611; 4,866,034 and 4,912,094 for structures and methods of isolation and synthesis). A structure of MPLA is disclosed in U.S. Pat. No. 4,987,237. Non-toxic diphosphoryl lipid A (DPLA) may also be used, for example OM-174, a lipid A analogue of bacterial origin containing a triacyl motif linked to a diglucosamine diphosphate backbone. Another class of useful compounds are synthetic lipid A analogue pseudo-dipeptides derived from amino acids linked to three fatty acid chains (see for example EP 1242365), such as OM-197-MP-AC, a water soluble synthetic acylated pseudo-dipeptide ($C_{55}H_{107}N_4O_{12}P$). Non-toxic TLR4 agonists include also those disclosed in EP1091928, PCT/FRO5/00575 or PCT/IB2006/050748. PCT/US2006/002906/WO 2006/083706; PCT/US 2006/003285/WO 2006/083792; PCT/US 2006/041865; PCT/US 2006/042051. TLR4 agonists also include synthetic compounds which signal through TLR4 other than those based on the lipid A core structure, for example an aminoalkyl glucosaminide 4-phosphate (see Evans J T et al. Expert Rev Vaccines. 2003 April; 2(2):219-29; or Persing et al. Trends Microbiol. 2002; 10(10 Suppl):S32-7. Review). Other examples include those described in Orr M T, Duthie M S, Windish H P, Lucas E A, Guderian J A, Hudson T E, Shaverdian N, O'Donnell J, Desbien A L, Reed S G, Coler R N. MyD88 and TRIF synergistic interaction is required for TH1-cell polarization with a synthetic TLR4 agonist adjuvant. Eur J Immunol. 2013 May 29. doi: 10.1002/eji.201243124; Lambert S L, Yang C F, Liu Z, Sweetwood R, Zhao J, Cheng L, Jin H, Woo J. Molecular and cellular response profiles induced by the TLR4 agonist-based adjuvant Glucopyranosyl Lipid A. PLoS One. 2012; 7(12): e51618. doi: 10.1371/journal.pone.0051618. Epub 2012 Dec. 28.

In some embodiments, the TLR agonist is a TLR5 agonist. Typically, the TLR5 agonist according to the invention is a flagellin polypeptide. As used herein, the term "flagellin" is intended to mean the flagellin contained in a variety of Gram-positive or Gram-negative bacterial species. Non-limiting sources of flagellins include but are not limited to *Escherichia*, e.g., *E. coli, Enterobacter, Erwinia, Klebsiella, Proteus, Salmonella*, e.g., *Salmonella enterica* serovar *Typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*. These examples are illustrative rather than limiting. The amino acid sequences and nucleotide sequences of flagellins are publically available in the NCBI Genbank, see for example Accession Nos. AAL20871, NP_310689, BAB58984, AAO85383, AAA27090, NP_461698, AAK58560, YP_001217666, YP_002151351, YP_001250079, AAA99807, CAL35450, AAN74969, and BAC44986. The flagellin sequences from these and other species are intended to be encompassed by the term flagellin as used herein. Therefore, the sequence differences between species are included within the meaning of the term. The term "flagellin polypeptide" is intended to a flagellin or a fragment thereof that retains the ability to bind and activate TLR5. Typically, the flagellin polypeptide according to the invention comprises the domains of flagellin involved in TLR5 signaling. The term "domain of flagellin" includes naturally occurring domain of flagellin and function conservative variants thereof "Function conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Examples of flagellin polypeptides include but are not limited to those described in U.S. Pat. Nos. 6,585,980; 6,130,082; 5,888,810; 5,618,533; and 4,886,748; U.S. Patent Publication No. US 2003/0044429 A1; and in the International Patent Application Publications n° WO 2008097016 and WO 2009156405 which are incorporated by reference. An exemplary *E. coli* O157:H7 flagellin is SEQ ID NO:1. An exemplary *S. typhimurium* flagellin is SEQ ID NO:2 or SEQ ID NO:3. Amino acid sequences at least about 90%, at least about 95%, at least about 97%, at least about 98% or at least about 99% identical to SEQ ID NO: 1 SEQ ID NO:2 or SEQ ID NO:3 can be used as flagellin polypeptides according to the invention. In another particular embodiment, of the TLR5 agonist is selected among flagellin recombinant proteins described in the International Patent Application WO2009156405 (which is incorporated by reference in its entirety). Accordingly, a flagellin polypeptide of the invention may comprise: a) a N-terminal peptide having at least 90% amino acid identity with the amino acid sequence starting from the amino acid residue located at position 1 of SEQ ID NO:3 and ending at an amino acid residue selected from the group consisting of any one of the amino acid residues located at positions 99 to 173 of SEQ ID NO:3; and b) a C-terminal peptide having at least 90% amino acid identity with the amino acid sequence starting at an amino acid residue selected from the group consisting of any one of the amino acid residues located at positions 401 to 406 of SEQ ID NO:3 and ending at the amino acid residue located at position 494 of SEQ ID NO:3, wherein: the said N-terminal peptide is directly linked to the said C-terminal peptide, or the said N-terminal peptide and the said C-terminal peptide are indirectly linked, one to the other, through a spacer chain. In another particular embodiment, said N-terminal peptide is selected from the group consisting of the amino acid sequences 1-99, 1-137, 1-160 and 1-173 of SEQ ID NO:3. In some embodiments, said C-terminal peptide is selected from the group consisting of the amino acid sequences 401-494 and 406-494 of SEQ ID NO:3. In some embodiments, said N-terminal and C-terminal peptides consist of the amino acid sequences 1-173 and 401-494 of SEQ ID NO:3, respectively. In some embodiments, said N-terminal and C-terminal peptides consist of the amino acid sequences 1-160 and 406-494 of SEQ ID NO:3, respectively. In some embodiments, said N-terminal and C-terminal peptides consist of the amino acid sequences 1-137 and 406-494 of SEQ ID NO:3, respectively. In some embodiments, said N-terminal peptide and the said C-terminal peptide are indirectly linked, one to the other, through an intermediate spacer chain consisting of a NH2-Gly-Ala-Ala-Gly-COOH (SEQ ID NO:4) peptide sequence. In some embodiments, the asparagine amino acid residue located at position 488 of SEQ ID NO:3 is replaced by a serine. In some embodiments, the flagellin polypeptide as above described comprises an additional methionine residue at the N-terminal end. Typically, the flagellin polypeptide according to the invention may be recombinantly produced by recombinant cells that have been transfected with a nucleic acid that encodes its amino acid sequence and allows its effective production within the transfected cells.

In some embodiments, the TLR agonist is a TLR7 agonist. For example, TLR7 agonists include, but are not limited to: imidazoquinoline-like molecules, imiquimod, resiquimod, gardiquimod, S-27609; and guanosine analogues such as loxoribine (7-allyl-7,8-dihydro-8-oxo-guanosine), 7-Thia-8-oxoguanosine and 7-deazaguanosine, UC-1V150, ANA975 (Anadys Pharmaceuticals), SM-360320 (Sumimoto), 3M-01 and 3M-03 (3M Pharmaceuticals) (see for example Gorden et al., J Immunology, 2005; Schön, Oncogene, 2008; Wu et al., PNAS 2007). TLR7 agonists include imidazoquinoline compounds; guanosine analogs; pyrimidinone compounds such as bropirimine and bropirimine analogs; and the like. Imidazoquinoline compounds that function as TLR7 ligands include, but are not limited to, imiquimod, (also known as Aldara, R-837, S-26308), and R-848 (also known as resiquimod, S-28463; having the chemical structure: 4-amino-2-ethoxymethyl-α,α.-dimethyl-1H-imidazol[4,5-c]quinoline-1-ethanol). Suitable imidazoquinoline agents include imidazoquinoline amines, imidazopyridine amines, 6,7-fused cycloalkylimidazopyridine amines, and 1,2 bridged imidazoquinoline amines. These compounds have been described in U.S. Pat. Nos. 4,689,338, 4,929,624, 5,238,944, 5,266,575, 5,268,376, 5,346,905, 5,352,784, 5,389,640, 5,395,937, 5,494,916, 5,482,936, 5,525,612, 6,039,969 and 6,110,929. Particular species of imidazoquinoline agents that are suitable for use in a subject method include R-848 (S-28463); 4-amino-2ethoxymethyl-α,α-dimethyl-1H-imidazo[4,5-c]quinoline-s-i-ethanol; and 1-(2-methylpropyl)-1H-imidazo[4,5-c]quinolin-4-amine (R-837 or Imiquimod). Also suitable for use is the compound 4-amino-2-(ethoxymethyl)-α,α-dimethyl-6,7,8,9-tetrahydro-1H-imidazo[4,5-c]quinoline-1-ethanol hydrate (see, e.g., BM-003 in Gorden et al. (2005). Guanosine analogs that function as TLR7 ligands include certain C8-substituted and N7,C8-disubstituted guanine ribonucleotides and deoxyribonucleotides, including, but not limited to, Loxoribine (7-allyl-8-oxoguanosine), 7-thia-8-oxo-guanosine (TOG), 7-deazaguanosine, and 7-deazadeoxyguanosine (Lee et ah, 2003). Bropirimine (PNU-54461), a 5-halo-6-phenyl-pyrimidinone, and bropirimine analogs are described in the literature and are also suitable for use. See, e.g., Vroegop et al. (1999). Additional examples of suitable C8-substituted guanosines include but are not limited to 8-mercaptoguanosine, 8-bromoguanosine, 8-methylguanosine, 8-oxo-7,8-dihydroguanosine, C8-arylamino-2'-deoxyguanosine, C8-propynyl-guanosine, C8- and N7-substituted guanine ribonucleosides such as 7-allyl-8-oxoguanosine (loxoribine) and 7-methyl-8-oxoguanosine, 8-aminoguanosine, 8-hydroxy-2'-deoxyguanosine, and 8-hydroxyguanosine. TLR7-selective agonists also include those shown in U.S. Patent Publication 2004/0171086. Additional suitable TLR7 agonists include, but are not limited to, 2-(ethoxymethyl)-1-(2-methylpropyl)-1H-imidazo[4,5-c]quinolin-4-amine (U.S. Pat. No. 5,389,640); 2-methyl-1-[2-(3-pyridin-3-ylpropoxy) ethyl]-1H-imidazo[4,5-c]quinolin-4-amine (WO 02/46193); N-(2-{2-[4-amino-2-(2-methoxyethyl)-1H-imidazo[4,5-c]quinolin-1-yl]ethoxy}ethyl-ethylN-methylcyclohexanecarboxamide (U.S. Patent Publication 2004/0171086); 1-[2-(benzyloxy)ethyl]-2-methyl-1H-imidazo[4,5-c]quinolin-4-amine (WO 02/46189); N-{8-[4-amino-2-(2-methyoxyethyl)-1H-imidazo[4,5-c]quinolin-1-yl]octyl}-N-phenylurea (U.S. Patent Publication 2004/0171086 (IRM5)); 2-butyl-1-[5-(methylsulfonyl)pentyl]-1H-imidazo[4,5-c]quinolin-4-amine (WO 02/46192); N-{3-[4-amino-2-(2-methoxyethyl)-1H-imidazo[4,5-c]quinolin-1-yl]propyl}-4-methylbenzenesulfonamide (U.S. Pat. No. 6,331,539); and N-[4-(4-amino-2-ethyl-1H-imidazo[4,5-c]quinolin-1-yl)butyl]cyclohexanecarboxamidecarboxamide (U.S. Patent Publication 2004/0171086 (IRM8)). Also suitable for use is the TLR7-selective agonist N-[4-(4-amino-2-ethyl-1H-imidazo[4,5-c]quinolin-1-yl)butyl-]methanesulfon-amide.

In some embodiments, the TLR agonist is a TLR8 agonist. TLR8-selective agonists include those in U.S. Patent Publication 2004/0171086. Such TLR8 selective agonist compounds include, but are not limited to, the compounds shown in U.S. Patent Publication No. 2004/0171086 that include N-{4-[4-amino-2-(2-methoxyethyl)-1H-imidazo[4,5-c]quinolin-1-yl]butyl}quinolin-3-carboxamide, N-{4-[4-amino-2-(2-methoxyethyl)-1H-imidazo[4,5-c]quinolin-1-yl]butyl}quinoxoline-2-carboxamide, and N-[4-(4-amino-2-propyl-1H-imidazo[4,5-c]quinolin-1-yl)butyl]morpholine-4-carboxamide. Other suitable TLR8-selective agonists include, but are not limited to, 2-propylthiazolo[4,5-c]quinolin-4-amine (U.S. Pat. No. 6,110,929); N1-[2-(4-amino-2-butyl-1H-imidazo[4,5-c][1,5]naphthyridin-1-yl)ethyl]-2-amino-4-methylpentanamide (U.S. Pat. No. 6,194,425); N1-[4-(4-amino-1H-imidazo[4,5-c]quinolin-1-yl)butyl]-2-phenoxy-benzamide (U.S. Pat. No. 6,451,810); N1-[2-(4-amino-2-butyl-1H-imidazo[4,5-c]quinolin-1-yl)ethyl]-1-propanesulfonamide (U.S. Pat. No. 6,331,539); N-{2-[2-(4-amino-2-ethyl-1H-imidazo[4,5-c]quinolin-1-yl)ethyoxy]ethyl}-N'~phenylurea (U.S. Patent Publication 2004/0171086); 1-{4-[3,5-dichlorophenyl)thio]butyl}-2-ethyl-1H-imidazo[4,5-c]quinolin-4~amine (U.S. Patent Publication 2004/0171086); N-{2-[4-amino-2-(ethoxymethyl)-1H-imidazo[4,5-c]quinolin-1-yl]ethyl}-N'-(3-cyanophenyl)urea (WO 00/76518 and U.S. Patent Publication No. 2004/0171086); and 4-amino-α,α-dimethyl-2-methoxyethyl-1H-imidazo[4,5-c]quinoline-1-ethanol (U.S. Pat. No. 5,389,640). Included for use as TLR8-selective agonists are the compounds in U.S. Patent Publication No. 2004/0171086. Also suitable for use is the compound 2-propylthiazolo-4,5-c]quinolin-4-amine.

In some embodiments, the TLR agonist is a TLR9 agonist. Examples of TLR9 agonists (include nucleic acids comprising the sequence 5'-CG-3' (a "CpG nucleic acid"), in certain aspects C is unmethylated. The terms "polynucleotide," and "nucleic acid," as used interchangeably herein in the context of TLR9 agonist molecules, refer to a polynucleotide of any length, and encompasses, inter alia, single- and double-stranded oligonucleotides (including deoxyribonucleotides, ribonucleotides, or both), modified oligonucleotides, and oligonucleosides, alone or as part of a larger nucleic acid construct, or as part of a conjugate with a non-nucleic acid molecule such as a polypeptide. Thus a TLR9 agonist may be, for example, single-stranded DNA (ssDNA), double-stranded DNA (dsDNA), single-stranded RNA (ssRNA) or double-stranded RNA (dsRNA). TLR9 agonists also encompass crude, detoxified bacterial (e.g., mycobacterial) RNA or DNA, as well as enriched plasmids enriched for a TLR9 agonist. In some embodimentss, a "TLR9 agonist-enriched plasmid" refers to a linear or circular plasmid that comprises or is engineered to comprise a greater number of CpG motifs than normally found in mammalian DNA. Examples of non-limiting TLR9 agonist-enriched plasmids are described in Roman et al. (1997). In general, a TLR9 agonist used in a subject composition comprises at least one unmethylated CpG motif. In some embodimentss, a TLR9 agonist comprises a central palindromic core sequence comprising at least one CpG sequence, where the central palindromic core sequence contains a phosphodiester backbone, and where the central palindromic core sequence is flanked on one or both sides by phosphorothioate backbone-containing polyguanosine sequences. In other embodiments, a TLR9 agonist comprises one or more TCG sequences at or near the 5' end of the nucleic acid; and at least two additional CG dinucleotides. In some of these embodiments, the at least two additional CG dinucleotides are spaced three nucleotides, two nucleotides, or one nucleotide apart. In some of these embodiments, the at least two additional CG dinucleotides are contiguous with one another. In some of these embodiments, the TLR9 agonist comprises (TCG)n, where n=1 to 3, at the 5' end of the nucleic acid. In other embodiments, the TLR9 agonist comprises (TCG)n, where n=1 to 3, and where the (TCG)n sequence is flanked by one nucleotide, two nucleotides, three nucleotides, four nucleotides, or five nucleotides, on the 5' end of the (TCG)n sequence. A TLR9 agonist of the present invention includes, but is not limited to, any of those described in U.S. Pat. Nos. 6,194,388; 6,207,646; 6,239,116; 6,339,068; and 6,406,705, 6,426,334 and 6,476,000, and published US Patent Applications US 2002/0086295, US 2003/0212028, and US 2004/0248837.

In some embodiments the TLR agonist is an antibody directed against the Toll-like receptor of interest, in such a way that said antibody activates the receptor. Antibodies can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies can be prepared and isolated using any technique that provides for the production of antibody molecules by continuous cell lines in culture. Techniques for production and isolation include but are not limited to the hybridoma technique; the human B-cell hybridoma technique; and the EBV-hybridoma technique. Alternatively, techniques described for the production of single chain antibodies (see, e.g., U.S. Pat. No. 4,946,778) can be adapted to produce anti-TLR single chain antibodies. The TLR agonist useful in practicing the present invention also include anti-TLR antibody fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to the TLR of interest. Humanized antibodies and antibody fragments thereof can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816, 397). The present invention also includes so-called single chain antibodies. The term "single domain antibody" (sdAb) or "VHH" refers to the single heavy chain variable domain of antibodies of the type that can be found in Camelid mammals which are naturally devoid of light chains. Such VHH are also called "Nanobody®". According to the invention, sdAb can particularly be llama sdAb. Then after raising antibodies as above described, the skilled man in the art can easily select those that are TLR agonists.

In some embodiments, the TLR agonist is an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library. The random sequence library is obtainable by combinatorial chemical synthesis of DNA or RNA. In this library, each member is a linear oligomer, eventually chemically modified, of a unique sequence. Then after raising aptamers directed against the TLR of interest as above described, the skilled man in the art can easily select those that are TLR agonists.

In some embodiments, the antibiotic is selected from the group consisting of aminoglycosides, beta lactams, quinolones or fluoroquinolones, macrolides, sulfonamides, sulfamethaxozoles, tetracyclines, streptogramins, oxazolidinones (such as linezolid), rifamycins, glycopeptides, polymixins, lipo-peptide antibiotics.

Tetracyclines belong to a class that shares a four-membered ring structure composed of four fused 6-membered (hexacyclic) rings. The tetracyclines exhibit their activity by inhibiting the binding of the aminoacyl tRNA to the 30S ribosomal subunit in susceptible bacteria. Tetracyclines for use in the invention include chlortetracycline, demeclocycline, doxycycline, minocycline, oxytetracycline, chlortetracycline, methacycline, mecocycline, tigecycline, limecycline, and tetracycline. The tetracyclines are effective against many known organisms including a-hemolytic streptococci, nonhemolytic streptococci, gram negative bacilli, rickettsiae, spirochetes, *Mycoplasma*, and *Chlamydia*.

Aminoglycosides are compounds derived from species of *Streptomyces* or *Micomonospora* bacteria and are primarily used to treat infections caused by gram-negative bacteria. Drugs belonging to this class all possess the same basic chemical structure, i.e., a central hexose or diaminohexose molecule to which two or more amino sugars are attached by a glycosidic bond. The aminoglycosides are bactericidal antibiotics that bind to the 30S ribosome and inhibit bacterial protein synthesis. They are active primarily against aerobic gram-negative bacilli and staphylococci. Aminoglycoside antibiotics for use in the invention include amikacin (Amikin®), gentamicin (Garamycin®), kanamycin (Kantrex®), neomycin (Mycifradin®), netilmicin (Netromycin®), paromomycin (Humatin®), streptomycin, and tobramycin (TOBI Solution®, TobraDex®).

Macrolides are a group of polyketide antibiotic drugs whose activity stems from the presence of a macrolide ring (a large 14-, 15-, or 16-membered lactone ring) to which one or more deoxy sugars, usually cladinose and desosamine, are attached. Macrolides are primarily bacteriostatic and bind to the 50S subunit of the ribosome, thereby inhibiting bacterial synthesis. Macrolides are active against aerobic and anaerobic gram positive cocci (with the exception of enterococci) and against gram-negative anaerobes. Macrolides for use in the invention include azithromycin (Zithromax®), clarithromycin (Biaxin®), dirithromycin (Dynabac®), erythromycin, clindamycin, josamycin, roxithromycin and lincomycin.

Ketolides belong to a class of semi-synthetic 14-membered ring macrolides in which the erythromycin macrolactone ring structure and the D-desosamine sugar attached at position 5 are retained, however, replacing the L-cladinose5 moiety and hydroxyl group at position 3 is a3-keto functional group. The ketolides bind to the 23S rRNA, and their mechanism of action is similar to that of macrolides (Zhanel, G. G., et al., *Drugs*, 2001; 61(4):443-98). The ketolides exhibit good activity against gram-positive aerobes and some gram-negative aerobes, and possess excellent activity against *Streptococcus* spp. including mefA and ermB-producing *Streptococcus pneumoniae*, and *Haemophilus influenzae*. Representative ketolides for use in the invention include telithromycin (formerly known as HMR-3647), HMR 3004, HMR 3647, cethromycin, EDP-420, and ABT-773.

Structurally, the quinolones possess a 1,4 dihydro-4-oxoquinolinyl moiety bearing an essential carboxyl group at position 3. Functionally, the quinolones inhibit prokaryotic type II topoisomerases, namely DNA gyrase and, in a few cases, topoisomerase IV, through direct binding to the bacterial chromosome. Quinolones for use in the invention span first, second, third and fourth generation quinolones, including fluoroquinolones. Such compounds include nalidixic acid, cinoxacin, oxolinic acid, flumequine, pipemidic acid, rosoxacin, norfloxacin, lomefloxacin, ofloxacin, enrofloxacin, ciprofloxacin, enoxacin, amifloxacin, fleroxacin, gatifloxacin, gemifloxacin, clinafloxacin, sitafloxacin, pefloxacin, rufloxacin, sparfloxacin, temafloxacin, tosufloxacin, grepafloxacin, levofloxacin, moxifloxacin, and trovafloxacin. Additional quinolones suitable for use in the invention include those described in Hooper, D., and Rubinstein, E., "*Quinolone Antimicrobial Agents, Vd Edition*", American Society of Microbiology Press, Washington D.C. (2004).

Drugs belonging to the sulfonamide class all possess a sulfonamide moiety, $SO_2NH_2$, or a substituted sulfonamide moiety, where one 15 of the hydrogens on the nitrogen is replaced by an organic substituent. Illustrative N-substituents include substituted or unsubstituted thiazole, pyrimidine, isoxazole, and other functional groups. Sulfonamide antibiotics all share a common structural feature, i.e., they are all benzene sulfonamides, 20 meaning that the sulfonamide functionality is directly attached to a benzene ring. The structure of sulfonamide antibiotics is similar to p-aminobenzoic acid (PABA), a compound that is needed in bacteria as a substrate for the enzyme, dihydropteroate synthetase, for the synthesis of tetrahydro-25 folic acid. The sulfonamides function as antibiotics by interfering with the metabolic processes in bacteria that require PABA, thereby inhibiting bacterial growth and activity. Sulfonamide antibiotics for use in the invention include the following: mafenide, phtalylsulfathiazole, succinylsulfathiazole, sulfacetamide, sulfadiazine, sulfadoxine, sulfamazone, sulfamethazine, sulfamethoxazole, sulfametopirazine, sulfametoxypiridazine, sulfametrol, sulfamonomethoxine, sulfamylon, sulfanilamide, sulfaquinoxaline, sulfasalazine, sulfathiazole, sulfisoxazole, sulfisoxazole diolamine, and sulfaguanidine.

All members of beta-lactams possess a beta-lactam ring and a carboxyl group, resulting in 55 similarities in both their pharmacokinetics and mechanism of action. The majority of clinically useful beta-lactams belong to either the penicillin group or the cephalosporin group, including cefamycins and oxacephems. The beta-lactams also include the carbapenems and monobactams. Generally speaking, beta-lactams inhibit bacterial cell wall synthesis. More specifically, these antibiotics cause 'nicks' in the peptidoglycan net of the cell wall that allow the bacterial protoplasm to flow from its protective net into the surrounding hypotonic medium. Fluid then accumulates in the naked 65 protoplast (a cell devoid of its wall), and it eventually bursts, leading to death of the organism. Mechanistically, beta-lactarns act by inhibiting D-alanyl-D-alanine transpeptidase activity by forming stable esters with the carboxyl of the open lactam ring attached to the hydroxyl group of the enzyme target site. Beta-lactams are extremely effective and typically are of low toxicity. As a group, these drugs are active against many gram-positive, gram-negative and anaerobic organisms. Drugs falling into this category include 2-(3-alanyl)clavam, 2-hydroxymethylclavam, 7-methoxycephalosporin, epithienamycin, acetyl-thienamycin, amoxicillin, apalcillin, aspoxicillin, azidocillin, azlocillin, aztreonam, bacampicillin, blapenem, carbenicillin, carfecillin, carindacillin, carpetimycin A and B, cefacetril, cefaclor, cefadroxil, cefalexin, cefaloglycin, cefaloridine, cefalotin, cefamandole, cefapirin, cefatrizine, cefazedone, cefazolin, cefbuperazone, cefcapene, cefdinir, cefditoren, cefepime, cefetamet, cefixime, cefinenoxime, cefinetazole, cefminox, cefmolexin, cefodizime, cefonicid, cefoperazone, ceforamide, cefoselis, cefotaxime, cefotetan, cefotiam, cefoxitin, cefozopran, cefpiramide, cefpirome, cefpodoxime, cefprozil, cefquinome, cefradine, cefroxadine, cefsulodin, ceftazidime, cefteram, ceftezole, ceftibuten, ceftizoxime, ceftriaxone, cefuroxime, cephalosporin C, cephamycin A, cephamycin C, cephalothin, chitinovorin A, chitinovorin B, chitinovorin C, ciclacillin, clometocillin, cloxacillin, cycloserine, deoxy pluracidomycin B and C, dicloxacillin, dihydro pluracidomycin C, epicillin, epithienamycin D, E, and F, ertapenem, faropenem, flomoxef, flucloxacillin, hetacillin, imipenem, lenampicillin, loracarbef, mecillinam, meropenem, metampicillin, meticillin (also referred to as methicillin), mezlocillin, moxalactam, nafcillin, northienamycin, oxacillin, panipenem, penamecillin, penicillin G, N, and V, phenethicillin, piperacillin, povampicillin, pivcefalexin, povmecillinam, pivmecillinam, pluracidomycin B, C, and D, propicillin, sarmoxicillin, sulbactam, sultamicillin, talampicillin, temocillin, terconazole, thienamycin, andticarcillin.

Over 400 natural antimicrobial peptides have been isolated and characterized. Based on chemical structure, these peptides may be classified into two main groups: linear and cyclic (R. E. Hancock et al, Adv. Microb. Physiol., 1995, 37: 135-137; H. Kleinkauf et al., Criti. Rev. Biotechnol., 198, 8: 1-32; D. Perlman and M. Bodansky, Annu Rev. Biochem., 1971, 40: 449-464. The mode of action for the majority of these peptides (both linear and cyclic) is believed to involve membrane disruption, leading to cell leakage (A. Mor, Drug Develop. Res., 2000, 50: 440-447). The linear peptides, such as magainins and melitting, exist mainly as a-helical amphipathic structures (containing segregated hydrophobic and hydrophilic moieties), or as β-helices as found in gramicidin A (GA). Cyclic peptides, which mainly adopt an amphipatic β-sheet structures can be further divided into two subgroups: those containing disulfide bonds, such as tachyplesin, and those that do not, such as gramicidin S (D. Audreu and L. Rivas, Biopolymers, 1998, 47: 415-433). Peptide antibiotics also fall into two classes: non-ribosomally synthesized peptides, such as the gramicicins, polymyxins, bacitracins, glycopeptides, etc., and ribosomally synthesized (natural) peptides. The former are often drastically modified and are largely produced by bacteria, whereas the latter are produced by all species of life (including bacteria) as a major component of the natural host defense molecules of these species. In certain embodiments, the peptide antibiotic is a lipopeptide antibiotic such as colistin, daptomycin, surfactin, friulimicin, aculeacin A, iturin A, and tsushimycin. [00162] Colistin (also called Colimycin) is a polymixin antibiotic discovered more than 50 years ago. It is a cyclic lipopeptide antibiotic which penetrates the cell wall of Gram negative bacteria by self-induced mechanism by chelating divalent ions. Colistin destabilizes the wall and can insinuate into it. Colistin basically perforates the cell wall, causing distortion of this structure and the release of intracellular constituents. Increasing multidrug resistance in Gram-negative bacteria, in particular *Pseudomonas aeruginosa, Acinetobacter baumannii*, and *Klebsiella pneumoniae*, presents a critical problem. Limited therapeutic options have forced infectious disease clinicians and microbiologists to reappraise the clinical application of Colistin. Colistin is associated with neurotoxicity and nephrotoxicity. Dosage regimen and novel formulation may be an answer to address the toxicity issue.

In some embodimentss, the TLR agonist of the invention is used in combination with Bactrim® which contains both SULFAMETHOXAZOLE AND TRIMETHOPRIME.

In some embodiments, the TLR agonist and the antibiotic are to be used simultaneous or sequentially within a given time. The antibiotic can be applied in either order, e.g. the antibiotic can be applied first and then the TLR agonist can be applied or vice versa. It is obvious that when a composition comprising both the antibiotic and TLR agonist is used both components will be applied at the same time. When used sequentially, different routes of administration could be envisaged. For example, the antibiotic may be administered to the subject via the oral route and the TLR agonist is administered to the subject via the intravenous route (e.g. TLR4 agonist) or via the intranasal route (e.g. TLR5 agonist).

Suitable preparations, e.g., substantially pure preparations of the agents described herein (i.e. the TLR agonists and antibiotics) may be combined with pharmaceutically acceptable carriers, diluents, solvents, excipients, etc., to produce an appropriate pharmaceutical composition.

In some embodimentss, the invention further provides a pharmaceutically acceptable composition comprising (i) at least one TLR agonist; (ii) at least one antibiotic whose activity is potentiated by the TLR agonist; and (iii) a pharmaceutically acceptable carrier or excipient. This pharmaceutical composition is thus particularly suitable for the treatment of a bacterial infection. The invention further provides a pharmaceutically acceptable unit dosage form containing a predetermined amount of an antibiotic and a predetermined amount of a TLR agonist, wherein the predetermined amounts are selected so that the TLR agonist potentiates the antibiotic when the unit dosage form is administered to a subject.

The term "pharmaceutically acceptable carrier, excipient, or vehicle" refers to a non-toxic carrier, excipient, or vehicle that does not destroy the pharmacological activity of the agent with which it is formulated. Pharmaceutically acceptable carriers, excipients, or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Solvents, dispersion media, coatings, antibacterial and antifungal agents, isotonic and absorption delaying agents, and the like, compatible with pharmaceutical administration may be included. Pharmaceutically acceptable salts of the agents of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glyco late, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal {e.g., sodium and potassium), alkaline earth metal {e.g., magnesium), ammonium and NNo(C1-4 alkyl)4 salts. This invention also envisions the quaternization of any basic nitrogen-containing groups of the compounds disclosed herein. Water or oil-soluble or dispersible products may be obtained by such quaternization.

It is to be understood that the pharmaceutical compositions of the invention, when administered to a subject, are preferably administered for a time and in an amount sufficient to treat the bacterial infection. In various embodiments of the invention an effective amount of the pharmaceutical composition is administered to a subject by any suitable route of administration including, but not limited to, intravenous, intramuscular, by inhalation (e.g., as an aerosol), intraocularly, orally, rectally, intradermally, by application to the skin, etc. Accordingly the pharmaceutical composition is formulated to be compatible with its intended route of administration. Solutions or suspensions used for parenteral {e.g., intravenous), intramuscular, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use typically include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), phosphate buffered saline (PBS), or Ringer's solution.

Sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In all cases, the composition should be sterile, if possible, and should be fluid to the extent that easy syringeability exists.

Preferred pharmaceutical formulations are stable under the conditions of manufacture and storage and must be preserved against the contaminating action of microorganisms such as bacteria and fungi. In general, the relevant carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prolonged absorption of injectable compositions can be brought about by including in the composition an agent which delays absorption, for example, aluminum monostearate and gelatin. Prolonged absorption of oral compositions can be achieved by various means including encapsulation.

Sterile injectable solutions can be prepared by incorporating the active compound in the required amount in an appropriate solvent with one or a combination of ingredients enumerated above, as required, followed by filtered sterilization. Preferably solutions for injection are free of endotoxin. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of oral solution (e.g. for pediatric purpose) tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Formulations for oral delivery may advantageously incorporate agents to improve stability within the gastrointestinal tract and/or to enhance absorption.

For administration by inhalation, the inventive compositions are preferably delivered in the form of an aerosol spray from a pressured container or dispenser which contains a suitable propellant, e.g., a gas such as carbon dioxide, or a nebulizer. Liquid or dry aerosol (e.g., dry powders, large porous particles, etc.) can be used. The present invention also contemplates delivery of compositions using a nasal spray.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For local delivery to the eye, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. [00313] The compounds can also be prepared in the form of suppositories (e.g., with conventional suppository bases such as cocoa butter and other glycerides) or retention enemas for rectal delivery.

In addition to the agents described above, in certain embodiments of the invention, the active compounds are prepared with carriers that will protect the compound against rapid elimination from the body, such as a controlled release formulation, including implants and microencapsulated delivery systems. Biodegradable, bio compatible polymers can be used, such as ethylene vinyl acetate, polyanhydrides, polyglycolic acid, collagen, polyorthoesters, polyethers, and polylactic acid. Methods for preparation of such formulations will be apparent to those skilled in the art. Certain of the materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811 and other references listed herein. Liposomes, including targeted liposomes (e.g., antibody targeted liposomes) and pegylated liposomes have been described (Hansen C B, et al., Biochim Biophys Acta. 1239(2):133-44, 1995; Torchilin V P, et al., Biochim Biophys Acta, 1511(2): 397-411, 2001; Ishida T, et al., FEBS Lett. 460(1): 129-33, 1999). One of ordinary skill in the art will appreciate that the materials and methods selected for preparation of a controlled release formulation, implant, etc., should be such as to retain activity of the compound. For example, it may be desirable to avoid excessive heating of polypeptides, which could lead to denaturation and loss of activity.

It is typically advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic index are preferred. While compounds that exhibit toxic side effects can be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. For any compound used in the method of the invention, the therapeutically effective dose (e.g., dose that is therapeutically effective to achieve a desired degree of antibiotic potentiation) can be estimated initially from cell culture assays. A dose can be formulated in animal models to achieve a circulating plasma concentration range that includes the IC50 (e.g., the concentration of the test compound which achieves a half-maximal inhibition of symptoms, half-maximal inhibition of growth or survival of an infectious agent, etc.) as determined in cell culture. Such information can be used to more accurately determine useful doses in humans. Levels in plasma can be measured, for example, by high performance liquid chromatography.

A therapeutically effective amount of a pharmaceutical composition typically ranges from about 0.001 to 100 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The pharmaceutical composition can be administered at various intervals and over different periods of time as required, e.g., multiple times per day, daily, every other day, once a week for between about 1 to 10 weeks, between 2 to 8 weeks, between about 3 to 7 weeks, about 4, 5, or 6 weeks, etc. The skilled artisan will appreciate that certain factors can influence the dosage and timing required to effectively treat a subject, including but not limited to the severity of the disease or disorder, previous and current treatments, the general health and/or age of the subject, and other diseases present. Generally, treatment of a subject with an inventive composition can include a single treatment or, in many cases, can include a series of treatments. It will be appreciated that a range of different dosage combinations (i.e., doses of the antibiotic and TLR agonist) can be used.

Exemplary doses include milligram or microgram amounts or even nanogram amounts of the inventive compounds per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram.) For local administration (e.g., intranasal), doses much smaller than these may be used. It is furthermore understood that appropriate doses depend upon the potency of the agent, and may optionally be tailored to the particular recipient, for example, through administration of increasing doses until a preselected desired response is achieved. It is understood that the specific dose level for any particular subject may depend upon a variety of factors including the activity of the specific compound employed, the age, body weight, general health, gender, and diet of the subject, the time of administration, the route of administration, the rate of excretion, any drug combination, and the degree of expression or activity to be modulated.

The present invention also provides pharmaceutical packs or kits comprising one or more containers (e.g., vials, ampoules, test tubes, flasks, or bottles) containing one or more ingredients of the inventive pharmaceutical compositions, for example, allowing for the simultaneous or sequential administration of the TLR agonist and antibiotic agent(s) it potentiates. Optionally associated with such container(s) can be a notice in the form prescribed by a governmental agency regulating the manufacture, use or sale of pharmaceutical products, which notice reflects approval by the agency of manufacture, use or sale for human administration. Different ingredients may be supplied in solid (e.g., lyophilized) or liquid form. Each ingredient will generally be suitable as aliquoted in its respective container or provided in a concentrated form. Kits may also include media for the reconstitution of lyophilized ingredients. The individual containers of the kit are preferably maintained in close confinement for commercial sale.

The invention will be further illustrated by the following figures and examples. However, these examples and figures should not be interpreted in any way as limiting the scope of the present invention.

FIGURES

FIG. 1 shows that the bacterial numbers can be reduced by a factor of 10 by applying one dose of a toll-like receptor ligand (i.e. LPS which is TLR 4 agonist or CpG which is a TLR9 agonist). The Left side: Colony forming units (cfu) per mesenteric lymph node during normal gut infection course, 24 and 72 h post infection. Right side: effect of antibiotic treatment and combination of antibiotic treatment with immune stimulating adjuvants (LPS and CpG).

Figure 2:
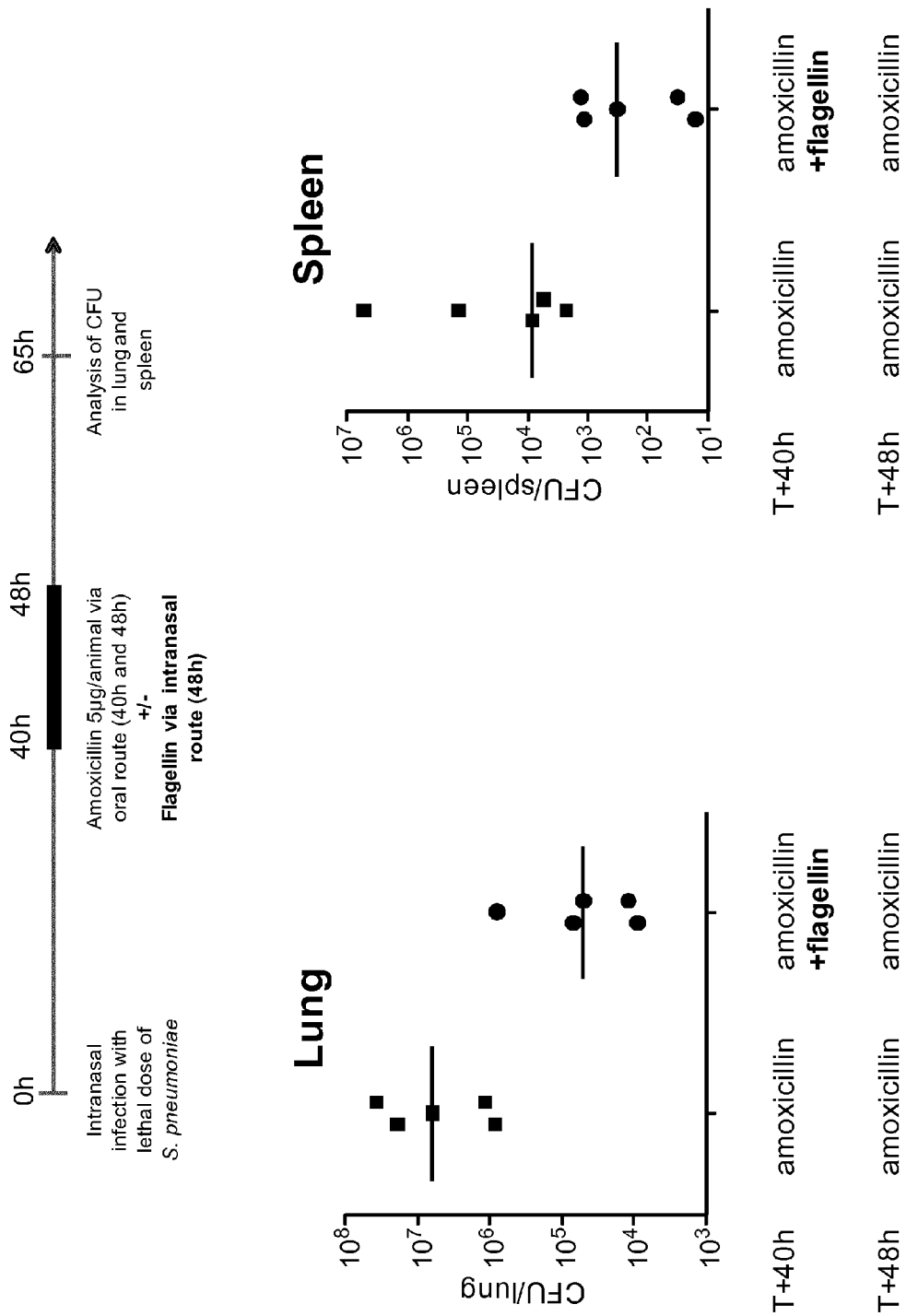

FIG. 2 shows that combining native flagellin and amoxicillin protects against respiratory infection. Animals were infected with a lethal dose of Streptococcus pneumoniae ($1\text{-}5\times10^6$ CFU of serotypel, clinical isolate E1586) and treated at 40 h and 48 h as depicted in the upper panel. Seventeen hours later (T=65 h), bacterial counts were defined by plating tissue homogenates. The Left side: bacterial counts per lung. Right side: bacterial counts per spleen.

Figure 3:
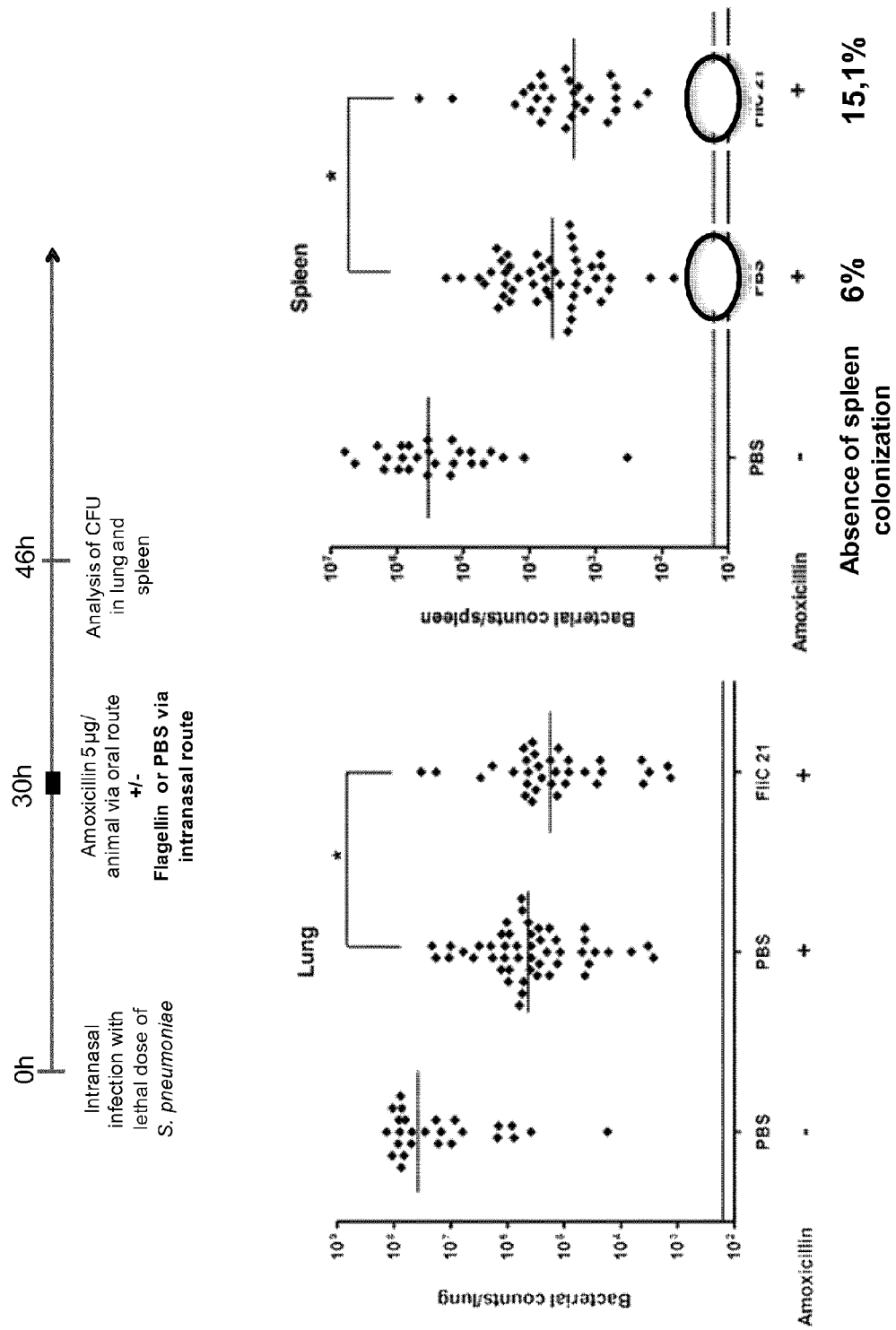

FIG. 3 shows that combining native flagellin and amoxicillin protects against respiratory infection. Animals were infected with a lethal dose of Streptococcus pneumoniae ($1\text{-}5\times10^6$ CFU of serotypel, clinical isolate E1586) and treated at 30 h as depicted in the upper panel. Sixteen hours later (T=46 h), bacterial counts were defined by plating tissue homogenates. The Left side: bacterial counts per lung. Right side: bacterial counts per spleen.

Figure 4:
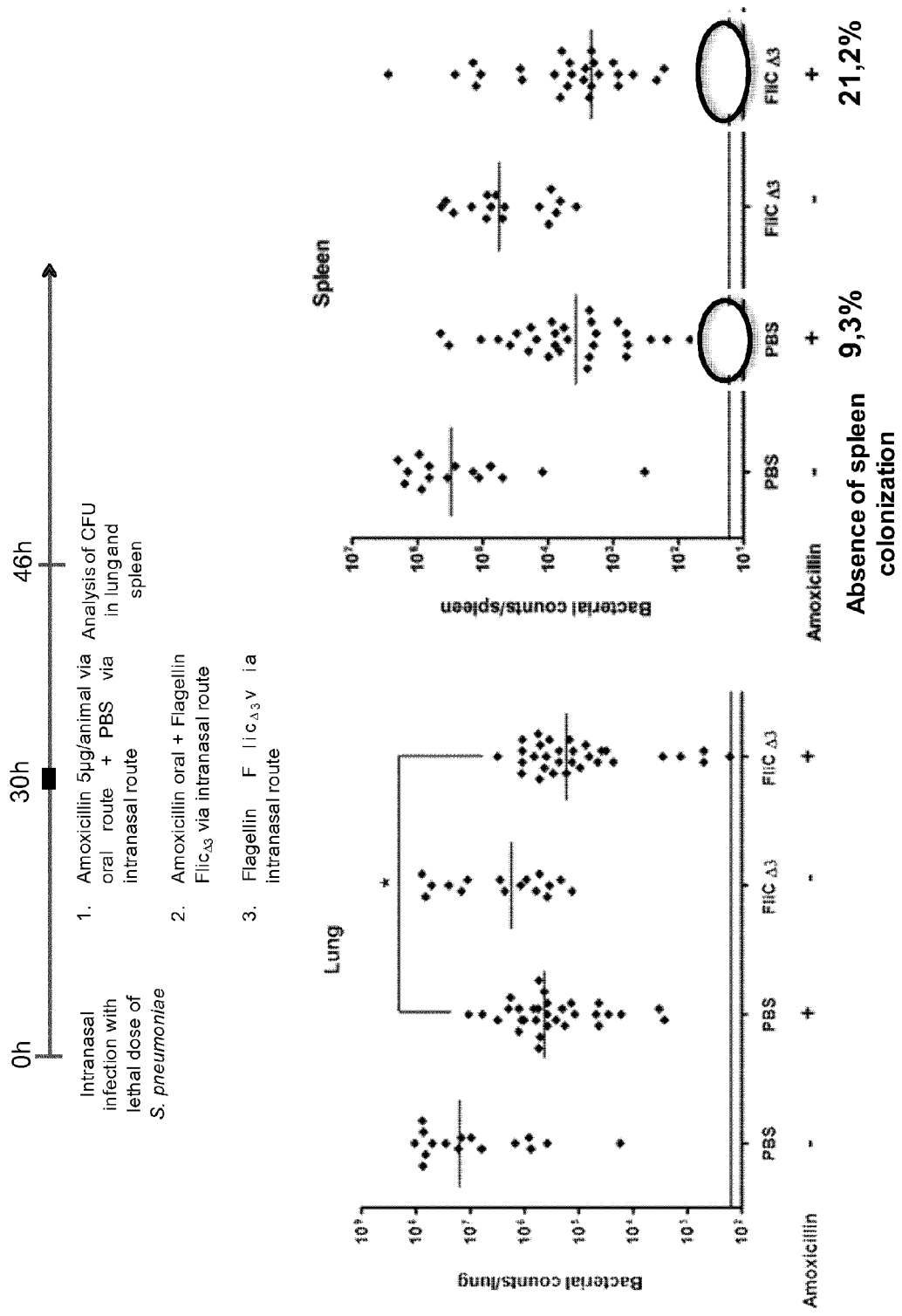

FIG. 4 shows that combining recombinant FliCΔ174-400 and amoxicillin protects against respiratory infection. Animals were infected with a lethal dose of Streptococcus pneumoniae ($1\text{-}5\times10^6$ CFU of serotypel, clinical isolate E1586) and treated at 30 h as depicted in the upper panel. Sixteen hours later (T=46 h), bacterial counts were defined by plating tissue homogenates. The Left side: bacterial counts per lung. Right side: bacterial counts per spleen.

Figure 5:
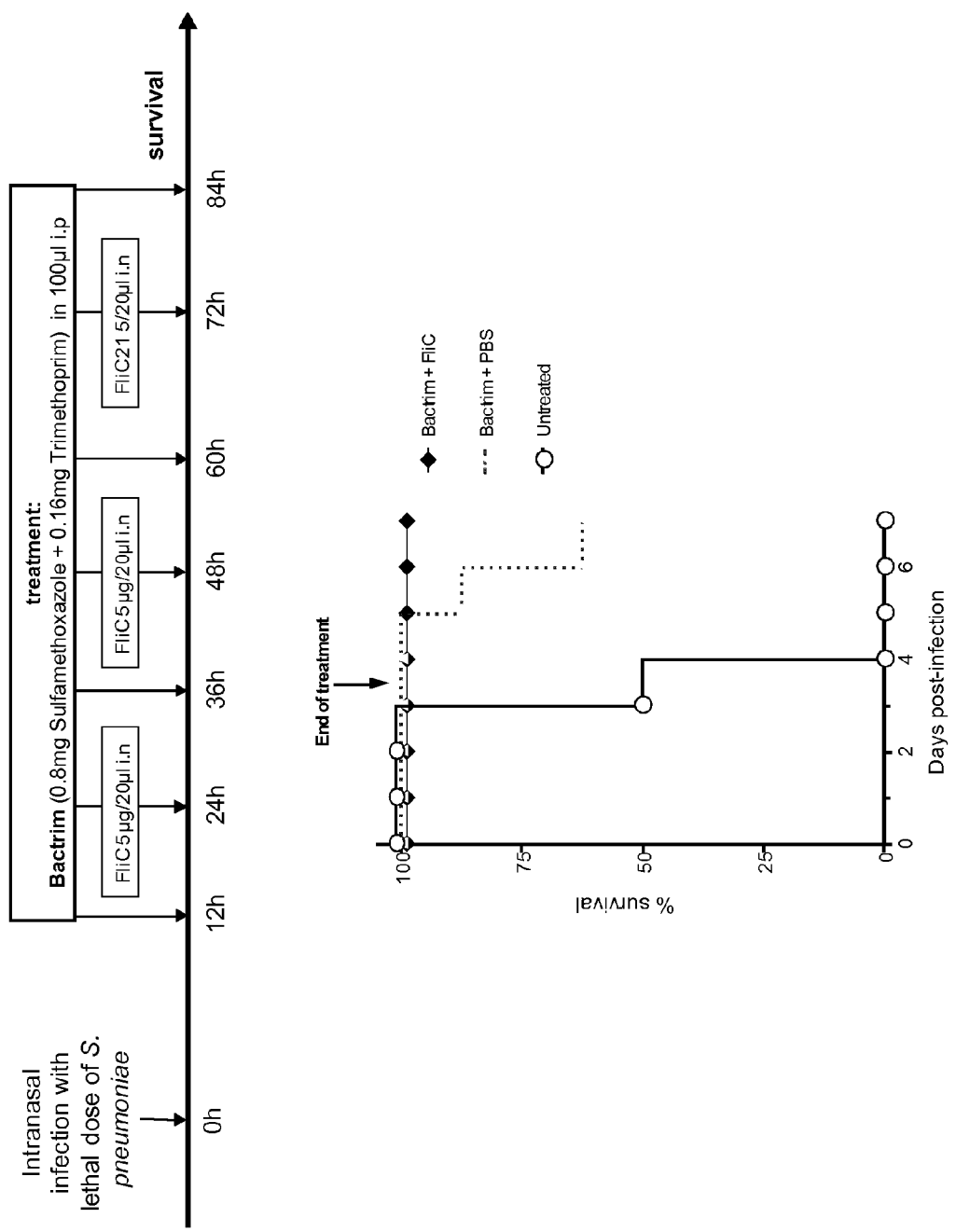

FIG. 5 shows that combining native Flagellin and Bactrim (Sulfamethoxazole+Trimetoprim) protects against respiratory infection. Animals were infected with a lethal dose of Streptococcus pneumoniae ($1\text{-}5\times10^6$ CFU of serotypel, clinical isolate E1586) and treated from 12 h to 84 h as depicted in the upper panel. Survival of animals was then analyzed during 5 days.

Figure 6:
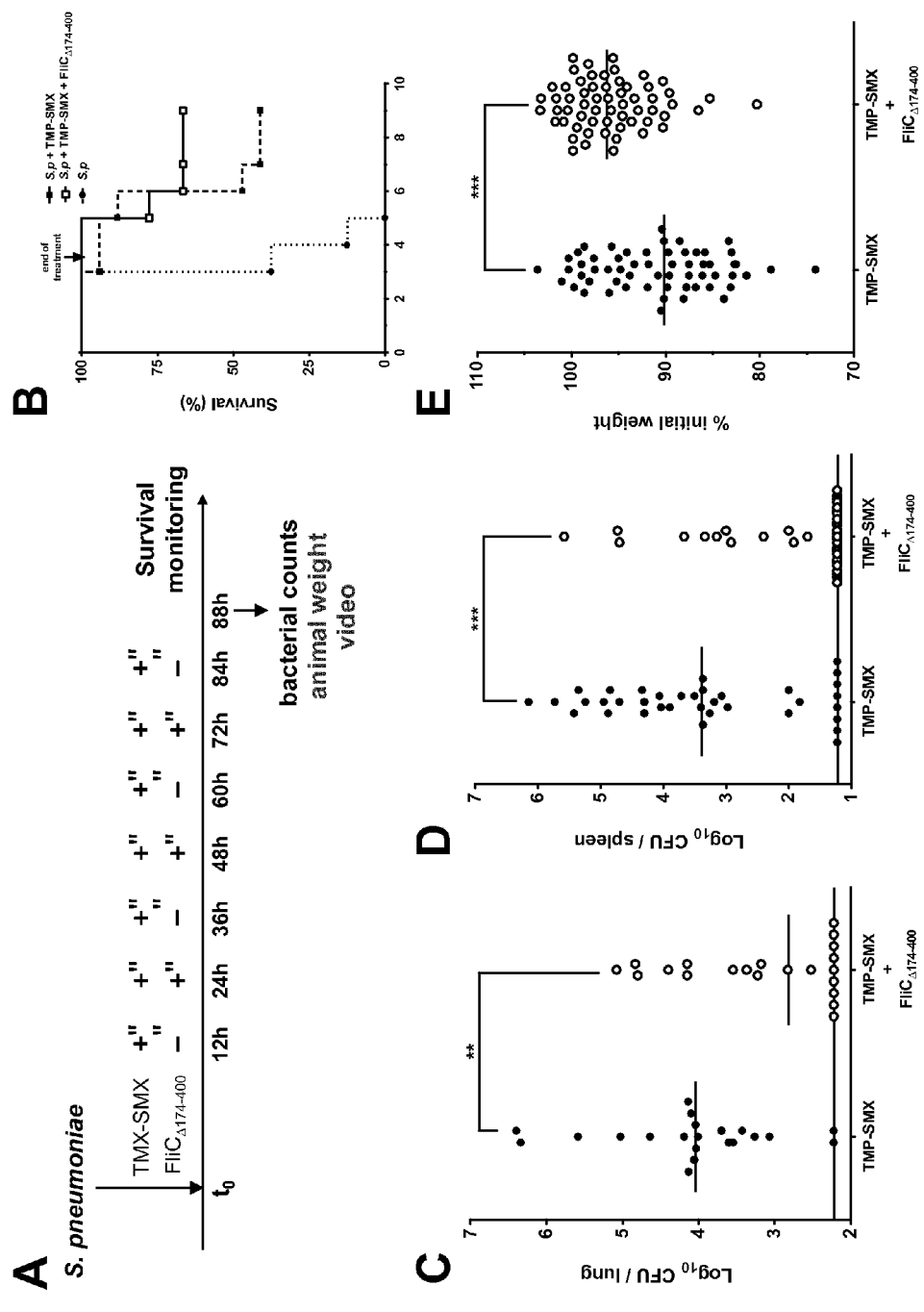

FIG. 6. Flagellin protects against S. pneumoniae infection during a treatment with co-trimoxasole. (A) S. pneumoniae-infected ($2\times10^6$ CFU) BALB/c mice were treated intraperitoneally with 4.8 mg bactrim, i.e. co-trimoxazole (TMP-SMX) and intranasally with 2.5 μg flagellin $FliC_{\Delta174\text{-}400}$ and analyzed as indicated. (B) Survival was monitored every 12 h for 9 days. (C, D) Bacterial counts in lung (C) and spleen (D) was determined by measuring CFU per tissue. Each dots represents CFU for an individual mouse. The solid line represents the threshold of detection. (E) The body weight of infected animals was measured and expressed relative to the initial weight. Statistical significance was determined with the non parametric test of Mann-Whitney (: $p<0.01$ and *: $p<0.001$).

Figure 7:
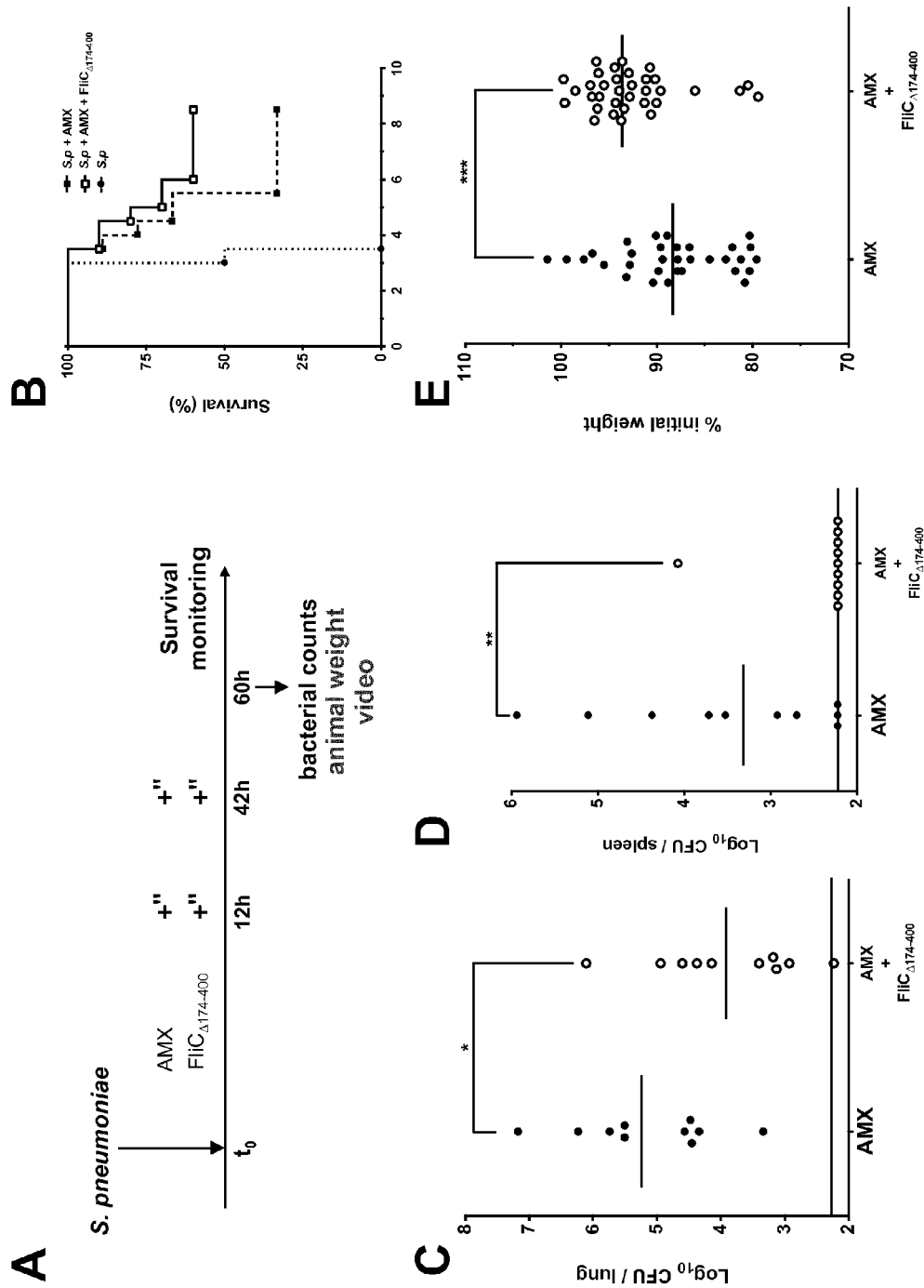

FIG. 7. Flagellin protects against S. pneumoniae infection during an amoxicillin treatment. (A) S. pneumoniae-infected ($2\times10^6$ CFU) BALB/c mice were treated intragastrically with 5 μg amoxicillin (AMX) and intranasally with 2.5 μg flagellin $FliC_{\Delta174\text{-}400}$ and analyzed as indicated. (B) Survival was monitored every 12 h for 9 days. (C, D) Bacterial counts in lung (C) and spleen (D) was determined by measuring CFU per tissue. Each dots represents CFU for an individual mouse. The solid line represents the threshold of detection. (E) The body weight of infected animals was measured and expressed relative to the initial weight. Statistical significance was determined with the non parametric test of Mann-Whitney (*: $p<0.05$, : $p<0.01$ and *: $p<0.001$).

Figure 8:
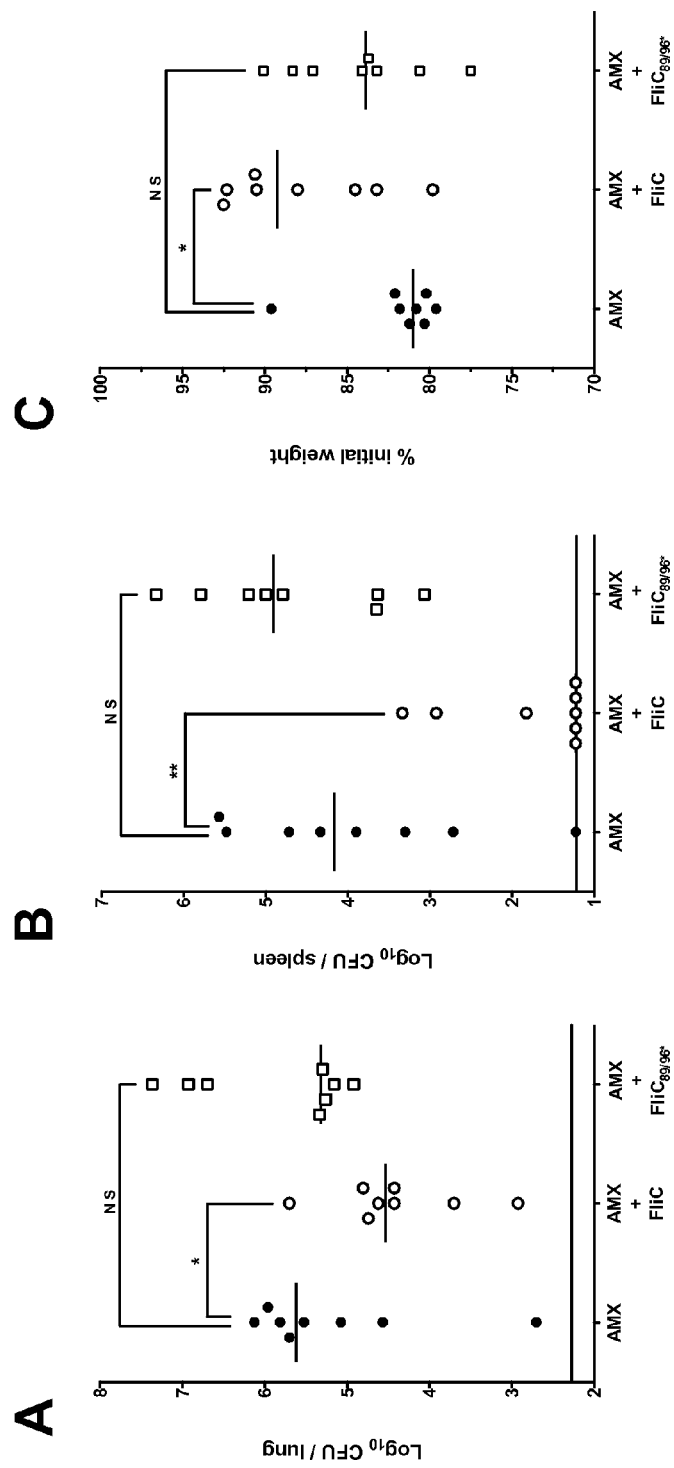

FIG. 8 Flagellin protection against S. pneumoniae infection is dependent of TLR5. S. pneumoniae-infected ($2\times10^6$ CFU) BALB/c mice were treated intragastricaly with 5 μg amoxicillin (AMX) and intranasally with 2.5 μg histidine-tagged native flagellin (FliC) or histidine-tagged mutated flagellin (FliC$_{89/96}$*) 12 h and 42 h post-infection. (A, B) Bacterial counts in lung (A) and spleen (B) was determined by measuring CFU per tissue 60 h post-infection. The solid line represents the threshold of detection. (C) The body weight of infected animals was measured and expressed relative to the initial weight. Statistical significance was determined with the non parametric test of Mann-Whitney (NS: non significant, *: $p<0.05$ and **: $p<0.01$).

Figure 9:
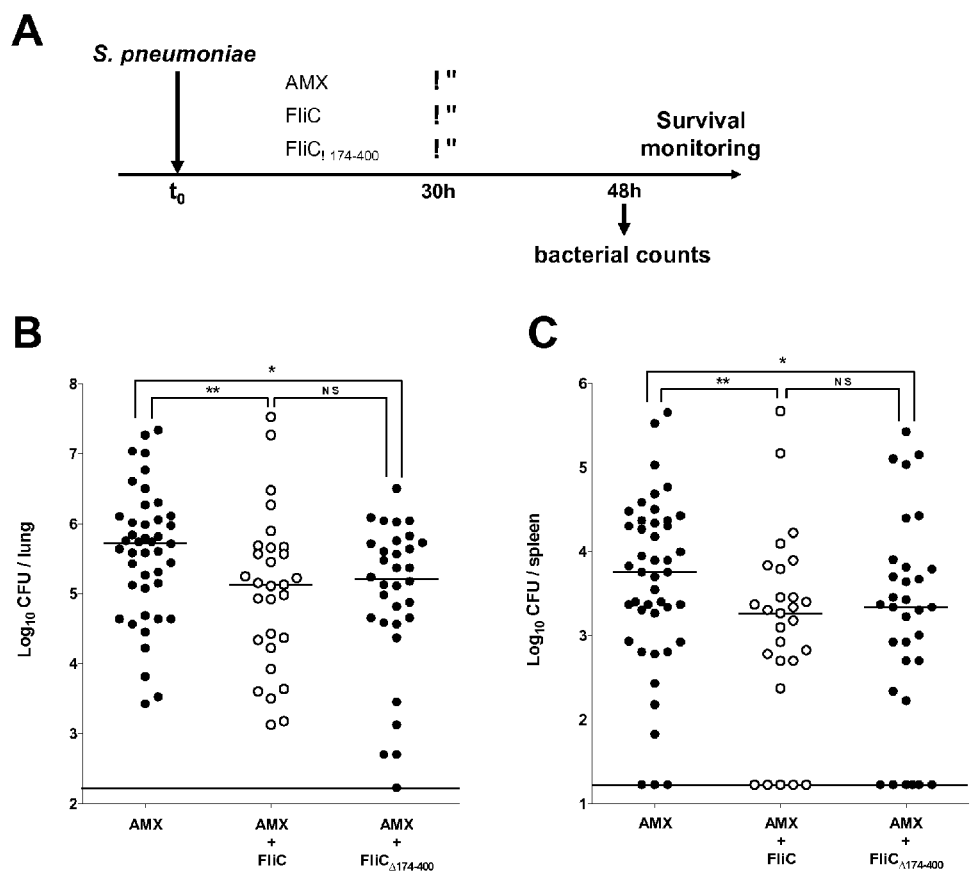

FIG. 9. Flagellin can also protects against late S. pneumoniae infection during an amoxicillin treatment. (A) S. pneumoniae-infected ($2\times10^6$ CFU) BALB/c mice were treated intragastrically with 5 μg amoxicillin (AMX) and intranasally by 2.5 μg recombinant flagellin FliC$_{\Delta174-400}$ or 5 μg native flagellin FliC 30 h post-infection as indicated. (B, C) Bacterial counts in lung (B) and spleen (C) was determined by measuring CFU per tissue 60 h post-infection. The solid line represents the threshold of detection. Statistical significance was determined with the non parametric test of Mann-Whitney (NS: non significant, *: $p<0.05$ and **: $p<0.01$).

EXAMPLE 1

Bacterial infections are a major health problem and pose a large economic burden on our society. Since their discovery, antibiotics have been used to treat bacterial infections. It is however becoming more evident, that antibiotics do not always perform to the extent they should. Some infections cannot be cleared, even if the pathogen is sensitive to the used antibiotic. This inability to completely kill all bacteria poses a severe problem once the antibiotic treatment is stopped, as the infection relapses and the patients fall ill anew. We propose a new therapeutic approach in which antibiotics are combined with innate immune stimulating adjuvants (i.e. Toll-like receptor agonists) to enhance the effect of the antibiotic treatment. We used our streptomycin pretreated mouse model for complicated Salmonella infections (Barthel, M., S. Hapfelmeier, L. Quintanilla-Martinez, M. Kremer, M. Rohde, M. Hogardt, K. Pfeffer, H. Russmann, and W. D. Hardt*. 2003. Pretreatment of mice with streptomycin provides a Salmonella enterica serovar Typhimurium colitis model that allows analysis of both pathogen and host. Infect Immun 71:2839-58; Endt, K., Maier, L., Käppeli, R., Barthel, M., Misselwitz, B., Kremer, M. and W. D. Hardt* (2012) Peroral Ciprofloxacin Therapy Impairs the Generation of a Protective Immune Response in a Mouse Model for Salmonella enterica Serovar Typhimurium Diarrhea, while Parenteral Ceftriaxone Therapy Does Not. Antimicrob Agents Chemother. 56(5):2295-304.) to mimic relapsing infections after antibiotic treatment and were able to improve the effectiveness of antibiotic treatment by using innate immune activating adjuvants. Simply treating infected mice with antibiotics is insufficient to clear Salmonella from the whole organism; some organs (i.e. lymph nodes) still carry high burdens of bacteria. These bacterial numbers can be reduced by a factor of 10 (and in a number of animals below the limit of detection) by applying one dose of a toll-like receptor ligand (i.e. LPS which is a TLR4 agonist or CpG which is a TLR9 agonist) (FIG. 1). This simultaneous activation of the innate immune system and antibiotic treatment is more efficient than antibiotic treatment alone, offering a potential therapy for complicated infections.

EXAMPLE 2

As antibiotic therapy becomes increasingly ineffective, modulating the innate immune system with TLR ligands may become a viable option to combat infections. The multiplicity of innate defense mechanisms induced by TLR signaling dampens development of bacterial resistance. It is important to stress out that TLR agonists like flagellin are effective in models of early infections when disease is initiated and when innate immunity is assumed to play its main role. Our aim is to determine whether antibiotics and flagellin may synergize. The rationale is to simultaneously attack bacteria via antibiotics and effectors of innate defenses and to cross-enhance activity of each drug. FIGS. 2-9 show that, in severe/advanced infection, the dual treatment with nasal flagellin and antibiotic (oral amoxicillin or intraperitoneal bactrim) significantly improves the outcome of pneumonia and invasive disease since the number of bacteria was significantly (e.g. 10-to-50 fold) reduced compared to the antibiotic therapy alone, thereby suggesting that the TLR5 agonist potentiates the activity of the antibiotic.

REFERENCES

Throughout this application, various references describe the state of the art to which this invention pertains. The disclosures of these references are hereby incorporated by reference into the present disclosure.

The invention claimed is:

1. A method for the treatment of *S. pneumoniae* infection in a subject in need thereof comprising administering to the subject a combination of a Toll-like receptor (TLR) agonist which is a flagellin polypeptide and an antibiotic which is amoxicillin or bactrim.

2. The method of claim 1, wherein the flagellin polypeptide has at least 90% of identity with SEQ ID NO:1, SEQ ID NO:2 or SEQ ID NO:3.

3. The method of claim 1, wherein the flagellin polypeptide comprises: a) a N-terminal peptide having at least 90% amino acid identity with the amino acid sequence starting from the amino acid residue located at position 1 of SEQ ID NO:3 and ending at an amino acid residue selected from the group consisting of any one of the amino acid residues located at positions 99 to 173 of SEQ ID NO:3; and b) a C-terminal peptide having at least 90% amino acid identity with the amino acid sequence starting at an amino acid residue selected from the group consisting of any one of the amino acid residues located at positions 401 to 406 of SEQ ID NO:3 and ending at the amino acid residue located at position 494 of SEQ ID NO:3, wherein: the said N-terminal peptide is directly linked to the C-terminal peptide, or the N-terminal peptide and the C-terminal peptide are indirectly linked, one to the other, through a spacer chain.

4. The method of claim 3, wherein the N-terminal peptide is selected from the group consisting of amino acid sequences 1-99, 1-137, 1-160 and 1-173 of SEQ ID NO:3.

5. The method of claim 3, wherein said C-terminal peptide is selected from the group consisting of amino acid sequences 401-494 and 406-494 of SEQ ID NO:3.

6. The method of claim 3, wherein said N-terminal and C-terminal peptides consist of amino acid sequences 1-173 and 401-494 of SEQ ID NO:3, respectively.

7. The method of claim 3, wherein said N-terminal and C-terminal peptides consist of amino acid sequences 1-160 and 406-494 of SEQ ID NO:3, respectively.

8. The method of claim 3, wherein said N-terminal and C-terminal peptides consist of amino acid sequences 1-137 and 406-494 of SEQ ID NO:3, respectively.

9. The method of claim 3, wherein said N-terminal peptide and said C-terminal peptide are indirectly linked, one to the other, through an intermediate spacer chain consisting of a NH2-Gly-Ala-Ala-Gly-COOH (SEQ ID NO:4) peptide sequence.

10. The method of claim 3, wherein an asparagine amino acid residue located at position 488 of SEQ ID NO:3 is replaced by a serine.

11. The method of claim 1 which is suitable for the clearance of a bacterium resistant to said antibiotic.

12. The method of claim 1, wherein the bacterial infection is due to a resistant or persistent bacterium.

13. The method of claim 1, wherein the *S. pneumoniae* infection is due to a bacterium that is resistant to treatment with said antibiotic alone.

\* \* \* \* \*

SEQUENCE LISTING

```
<160> NUMBER OF SEQ ID NOS: 4

<210> SEQ ID NO 1
<211> LENGTH: 585
<212> TYPE: PRT
<213> ORGANISM: Escherichia coli

<400> SEQUENCE: 1

Met Ala Gln Val Ile Asn Thr Asn Ser Leu Ser Leu Ile Thr Gln Asn
1               5                   10                  15
```

```
Asn Ile Asn Lys Asn Gln Ser Ala Leu Ser Ser Ser Ile Glu Arg Leu
         20                  25                  30
Ser Ser Gly Leu Arg Ile Asn Ser Ala Lys Asp Asp Ala Ala Gly Gln
         35                  40                  45
Ala Ile Ala Asn Arg Phe Thr Ser Asn Ile Lys Gly Leu Thr Gln Ala
 50                  55                  60
Ala Arg Asn Ala Asn Asp Gly Ile Ser Val Ala Gln Thr Thr Glu Gly
 65                  70                  75                  80
Ala Leu Ser Glu Ile Asn Asn Asn Leu Gln Arg Ile Arg Glu Leu Thr
                 85                  90                  95
Val Gln Ala Thr Thr Gly Thr Asn Ser Asp Ser Asp Leu Asp Ser Ile
             100                 105                 110
Gln Asp Glu Ile Lys Ser Arg Leu Asp Glu Ile Asp Arg Val Ser Gly
         115                 120                 125
Gln Thr Gln Phe Asn Gly Val Asn Val Leu Ala Lys Asp Gly Ser Met
         130                 135                 140
Lys Ile Gln Val Gly Ala Asn Asp Gly Glu Thr Ile Thr Ile Asp Leu
145                 150                 155                 160
Lys Lys Ile Asp Ser Asp Thr Leu Gly Leu Asn Gly Phe Asn Val Asn
                 165                 170                 175
Gly Lys Gly Thr Ile Thr Asn Lys Ala Ala Thr Val Ser Asp Leu Thr
             180                 185                 190
Ser Ala Gly Ala Lys Leu Asn Thr Thr Thr Gly Leu Tyr Asp Leu Lys
         195                 200                 205
Thr Glu Asn Thr Leu Leu Thr Thr Asp Ala Ala Phe Asp Lys Leu Gly
         210                 215                 220
Asn Gly Asp Lys Val Thr Val Gly Gly Val Asp Tyr Thr Tyr Asn Ala
225                 230                 235                 240
Lys Ser Gly Asp Phe Thr Thr Thr Lys Ser Thr Ala Gly Thr Gly Val
                 245                 250                 255
Asp Ala Ala Ala Gln Ala Ala Asp Ser Ala Ser Lys Arg Asp Ala Leu
             260                 265                 270
Ala Ala Thr Leu His Ala Asp Val Gly Lys Ser Val Asn Gly Ser Tyr
         275                 280                 285
Thr Thr Lys Asp Gly Thr Val Ser Phe Glu Thr Asp Ser Ala Gly Asn
         290                 295                 300
Ile Thr Ile Gly Gly Ser Gln Ala Tyr Val Asp Asp Ala Gly Asn Leu
305                 310                 315                 320
Thr Thr Asn Asn Ala Gly Ser Ala Ala Lys Ala Asp Met Lys Ala Leu
                 325                 330                 335
Leu Lys Ala Ala Ser Glu Gly Ser Asp Gly Ala Ser Leu Thr Phe Asn
             340                 345                 350
Gly Thr Glu Tyr Thr Ile Ala Lys Ala Thr Pro Ala Thr Thr Thr Pro
         355                 360                 365
Val Ala Pro Leu Ile Pro Gly Gly Ile Thr Tyr Gln Ala Thr Val Ser
         370                 375                 380
Lys Asp Val Val Leu Ser Glu Thr Lys Ala Ala Ala Thr Ser Ser
385                 390                 395                 400
Ile Thr Phe Asn Ser Gly Val Leu Ser Lys Thr Ile Gly Phe Thr Ala
                 405                 410                 415
Gly Glu Ser Ser Asp Ala Ala Lys Ser Tyr Val Asp Asp Lys Gly Gly
             420                 425                 430
Ile Thr Asn Val Ala Asp Tyr Thr Val Ser Tyr Ser Val Asn Lys Asp
```

```
                435                 440                 445
Asn Gly Ser Val Thr Val Ala Gly Tyr Ala Ser Ala Thr Asp Thr Asn
    450                 455                 460

Lys Asp Tyr Ala Pro Ala Ile Gly Thr Ala Val Asn Val Asn Ser Ala
465                 470                 475                 480

Gly Lys Ile Thr Thr Glu Thr Thr Ser Ala Gly Ser Ala Thr Thr Asn
                485                 490                 495

Pro Leu Ala Ala Leu Asp Asp Ala Ile Ser Ser Ile Asp Lys Phe Arg
            500                 505                 510

Ser Ser Leu Gly Ala Ile Gln Asn Arg Leu Asp Ser Ala Val Thr Asn
            515                 520                 525

Leu Asn Asn Thr Thr Thr Asn Leu Ser Glu Ala Gln Ser Arg Ile Gln
        530                 535                 540

Asp Ala Asp Tyr Ala Thr Glu Val Ser Asn Met Ser Lys Ala Gln Ile
545                 550                 555                 560

Ile Gln Gln Ala Gly Asn Ser Val Leu Ala Lys Ala Asn Gln Val Pro
                565                 570                 575

Gln Gln Val Leu Ser Leu Leu Gln Gly
            580                 585

<210> SEQ ID NO 2
<211> LENGTH: 495
<212> TYPE: PRT
<213> ORGANISM: Salmonella typhimurium

<400> SEQUENCE: 2

Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ala
                85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Thr Leu Asn Val Gln
                165                 170                 175

Gln Lys Tyr Lys Val Ser Asp Thr Ala Ala Thr Val Thr Gly Tyr Ala
            180                 185                 190

Asp Thr Thr Ile Ala Leu Asp Asn Ser Thr Phe Lys Ala Ser Ala Thr
        195                 200                 205

Gly Leu Gly Gly Thr Asp Gln Lys Ile Asp Gly Asp Leu Lys Phe Asp
    210                 215                 220
```

```
Asp Thr Thr Gly Lys Tyr Tyr Ala Lys Val Thr Val Thr Gly Gly Thr
225                 230                 235                 240

Gly Lys Asp Gly Tyr Tyr Glu Val Ser Val Asp Lys Thr Asn Gly Glu
            245                 250                 255

Val Thr Leu Ala Gly Gly Ala Thr Ser Pro Leu Thr Gly Gly Leu Pro
        260                 265                 270

Ala Thr Ala Thr Glu Asp Val Lys Asn Val Gln Val Ala Asn Ala Asp
    275                 280                 285

Leu Thr Glu Ala Lys Ala Ala Leu Thr Ala Ala Gly Val Thr Gly Thr
290                 295                 300

Ala Ser Val Val Lys Met Ser Tyr Thr Asp Asn Asn Gly Lys Thr Ile
305                 310                 315                 320

Asp Gly Gly Leu Ala Val Lys Val Gly Asp Asp Tyr Tyr Ser Ala Thr
            325                 330                 335

Gln Asn Lys Asp Gly Ser Ile Ser Ile Asn Thr Thr Lys Tyr Thr Ala
            340                 345                 350

Asp Asp Gly Thr Ser Lys Thr Ala Leu Asn Lys Leu Gly Gly Ala Asp
        355                 360                 365

Gly Lys Thr Glu Val Val Ser Ile Gly Gly Lys Thr Tyr Ala Ala Ser
370                 375                 380

Lys Ala Glu Gly His Asn Phe Lys Ala Gln Pro Asp Leu Ala Glu Ala
385                 390                 395                 400

Ala Ala Thr Thr Thr Glu Asn Pro Leu Gln Lys Ile Asp Ala Ala Leu
            405                 410                 415

Ala Gln Val Asp Thr Leu Arg Ser Asp Leu Gly Ala Val Gln Asn Arg
        420                 425                 430

Phe Asn Ser Ala Ile Thr Asn Leu Gly Asn Thr Val Asn Asn Leu Thr
    435                 440                 445

Ser Ala Arg Ser Arg Ile Glu Asp Ser Asp Tyr Ala Thr Glu Val Ser
450                 455                 460

Asn Met Ser Arg Ala Gln Ile Leu Gln Gln Ala Gly Thr Ser Val Leu
465                 470                 475                 480

Ala Gln Ala Asn Gln Val Pro Gln Asn Val Leu Ser Leu Leu Arg
            485                 490                 495

<210> SEQ ID NO 3
<211> LENGTH: 494
<212> TYPE: PRT
<213> ORGANISM: Salmonella typhimurium

<400> SEQUENCE: 3

Ala Gln Val Ile Asn Thr Asn Ser Leu Ser Leu Leu Thr Gln Asn Asn
1               5                   10                  15

Leu Asn Lys Ser Gln Ser Ala Leu Gly Thr Ala Ile Glu Arg Leu Ser
            20                  25                  30

Ser Gly Leu Arg Ile Asn Ser Ala Lys Asp Asp Ala Ala Gly Gln Ala
        35                  40                  45

Ile Ala Asn Arg Phe Thr Ala Asn Ile Lys Gly Leu Thr Gln Ala Ser
    50                  55                  60

Arg Asn Ala Asn Asp Gly Ile Ser Ile Ala Gln Thr Thr Glu Gly Ala
65                  70                  75                  80

Leu Asn Glu Ile Asn Asn Asn Leu Gln Arg Val Arg Glu Leu Ala Val
                85                  90                  95

Gln Ser Ala Asn Ser Thr Asn Ser Gln Ser Asp Leu Asp Ser Ile Gln
            100                 105                 110
```

Ala Glu Ile Thr Gln Arg Leu Asn Glu Ile Asp Arg Val Ser Gly Gln
            115                 120                 125

Thr Gln Phe Asn Gly Val Lys Val Leu Ala Gln Asp Asn Thr Leu Thr
    130                 135                 140

Ile Gln Val Gly Ala Asn Asp Gly Glu Thr Ile Asp Ile Asp Leu Lys
145                 150                 155                 160

Gln Ile Asn Ser Gln Thr Leu Gly Leu Asp Thr Leu Asn Val Gln Gln
                165                 170                 175

Lys Tyr Lys Val Ser Asp Thr Ala Ala Thr Val Thr Gly Tyr Ala Asp
            180                 185                 190

Thr Thr Ile Ala Leu Asp Asn Ser Thr Phe Lys Ala Ser Ala Thr Gly
        195                 200                 205

Leu Gly Gly Thr Asp Gln Lys Ile Asp Gly Asp Leu Lys Phe Asp Asp
    210                 215                 220

Thr Thr Gly Lys Tyr Tyr Ala Lys Val Thr Val Thr Gly Gly Thr Gly
225                 230                 235                 240

Lys Asp Gly Tyr Tyr Glu Val Ser Val Asp Lys Thr Asn Gly Glu Val
                245                 250                 255

Thr Leu Ala Gly Gly Ala Thr Ser Pro Leu Thr Gly Gly Leu Pro Ala
            260                 265                 270

Thr Ala Thr Glu Asp Val Lys Asn Val Gln Val Ala Asn Ala Asp Leu
        275                 280                 285

Thr Glu Ala Lys Ala Ala Leu Thr Ala Ala Gly Val Thr Gly Thr Ala
    290                 295                 300

Ser Val Val Lys Met Ser Tyr Thr Asp Asn Asn Gly Lys Thr Ile Asp
305                 310                 315                 320

Gly Gly Leu Ala Val Lys Val Gly Asp Asp Tyr Tyr Ser Ala Thr Gln
                325                 330                 335

Asn Lys Asp Gly Ser Ile Ser Ile Asn Thr Thr Lys Tyr Thr Ala Asp
            340                 345                 350

Asp Gly Thr Ser Lys Thr Ala Leu Asn Lys Leu Gly Gly Ala Asp Gly
        355                 360                 365

Lys Thr Glu Val Val Ser Ile Gly Gly Lys Thr Tyr Ala Ala Ser Lys
    370                 375                 380

Ala Glu Gly His Asn Phe Lys Ala Gln Pro Asp Leu Ala Glu Ala Ala
385                 390                 395                 400

Ala Thr Thr Thr Glu Asn Pro Leu Gln Lys Ile Asp Ala Ala Leu Ala
                405                 410                 415

Gln Val Asp Thr Leu Arg Ser Asp Leu Gly Ala Val Gln Asn Arg Phe
            420                 425                 430

Asn Ser Ala Ile Thr Asn Leu Gly Asn Thr Val Asn Asn Leu Thr Ser
        435                 440                 445

Ala Arg Ser Arg Ile Glu Asp Ser Asp Tyr Ala Thr Glu Val Ser Asn
    450                 455                 460

Met Ser Arg Ala Gln Ile Leu Gln Gln Ala Gly Thr Ser Val Leu Ala
465                 470                 475                 480

Gln Ala Asn Gln Val Pro Gln Asn Val Leu Ser Leu Leu Arg
                485                 490

<210> SEQ ID NO 4
<211> LENGTH: 4
<212> TYPE: PRT
<213> ORGANISM: Artificial
<220> FEATURE:

```
<223> OTHER INFORMATION: Synthetic peptide linker

<400> SEQUENCE: 4

Gly Ala Ala Gly
1
```